US008093231B2

(12) United States Patent
Allen et al.

(10) Patent No.: US 8,093,231 B2
(45) Date of Patent: Jan. 10, 2012

(54) SULFONYLETHYL PHOSPHORODIAMIDATES

(75) Inventors: David R. Allen, Oak Brook, IL (US);
Wenli Ma, Mountain View, CA (US);
Brian T. Peterson, San Jose, CA (US);
Louise Robinson, San Carlos, CA (US);
Steven R. Schow, Redwood City, CA (US); Songyuan Shi, Fremont, CA (US);
Reyna J. Simon, Los Gatos, CA (US);
Kevin T. Weber, Fremont, CA (US);
Michael M. Wick, Woodside, CA (US)

(73) Assignee: Telik, Inc., Palo Alto, CA (US)

( * ) Notice: Subject to any disclaimer, the term of this patent is extended or adjusted under 35 U.S.C. 154(b) by 0 days.

(21) Appl. No.: 11/779,234

(22) Filed: Jul. 17, 2007

(65) Prior Publication Data

US 2008/0039429 A1 Feb. 14, 2008

Related U.S. Application Data

(62) Division of application No. 11/134,218, filed on May 20, 2005, now Pat. No. 7,262,182.

(60) Provisional application No. 60/573,532, filed on May 12, 2004, provisional application No. 60/588,436, filed on Jul. 16, 2004.

(51) Int. Cl.
*A61K 31/66* (2006.01)
*A61K 35/00* (2006.01)
*C07F 9/02* (2006.01)

(52) U.S. Cl. ............... 514/102; 514/114; 558/157

(58) Field of Classification Search ............ 514/102, 514/114; 558/157
See application file for complete search history.

(56) References Cited

U.S. PATENT DOCUMENTS

| | | | | |
|---|---|---|---|---|
| 5,545,621 A * | 8/1996 | Kauvar et al. | | 514/18 |
| 5,556,942 A | 9/1996 | Kauvar et al. | | |
| 6,506,739 B1 * | 1/2003 | Herr et al. | | 514/140 |
| 6,667,330 B2 * | 12/2003 | Wang et al. | | 514/367 |

FOREIGN PATENT DOCUMENTS

| WO | WO 95/09865 | 4/1995 |
|---|---|---|
| WO | WO 95/09866 | 4/1995 |
| WO | WO 01/83496 | 11/2001 |
| WO | WO 2005/118601 A2 | 12/2005 |
| WO | WO 2005/118601 A3 | 4/2006 |

OTHER PUBLICATIONS

Cited ref_thiol amino acid_Google Schloar search.*
Chul-Hoon Kwon et al., "Chemically Stable, Lipophilic Prodrugs of Phosphoramide Mustard as Potential Anticancer Agents" *J. Med. Chem.* (1991) 34:588-592.
Yuan-Wan Sun et al., "Utilization of sufonylethyl groups in the design of nucleotide prodrugs" *Proc. Am. Assn. Cancer Res.* (2002) 43:208 (Abstract No. 1041).
Monish Jain et al. "1,2-Benzisoxazole Phosphorodiamidates as Novel Anticancer Prodrugs Requiring Bioreductive Activation" *J. Med. Chem.* (2002) 46:5428-5436.
Monish Jain et al. "Sulfonyl-Containing Aldophosphamide Analogues as Novel Anticancer Prodrugs Targeted against cyclophosphamide-Resistant Tumor Cell Lines" *J. Med. Chem.* (2004) 3843-3852 Published on the web Jun. 17, 2004 and in print Jul. 15, 2004.
Jain M et al:"Sulfonyl-containing aldophosphamide analogues as novel anticancer prodrugs targeted against cyclophosphamide-resistant tumor cell lines." Journal of Medicinal Chemistry, vol. 47,No. 15, Jul. 15, 2004, pp. 3843-3852, XP002354374 ISSN: 0022-2623 Chart 2 on p. 3844 Schemes 3, 4 & 5 on p. 3845, steps (c).
Rosario L A et al:"Cellular response to a glutathione 5-transferase P1-1 activated prodrug." Molecular Pharmacology, vol. 58,No. 1, Jul. 2000, pp. 167-174, XP002354375 ISSN: 0026-895X cited in the application figure 1.
Satyam A et al:"Design, Synthesis, and Evaluation of Latent Alkylating Agents activated by Glutathione S-Transferase" Journal of Medicinal Chemistry, vol. 39,1996, pp. 1736-1747, XP002351413 ISSN: 0022-2623 Compounds 2-5.
Ciaccio P J et al: "Modulation of detoxification gene expression in human colon HT29 cells byglutathione-S-transferase inhibitors"Molecular Pharmacology, vol. 48,No. 4, Oct. 1, 1995, pp. 639-647, XP000601686 ISSN: 0026-895X TER 286.
Lyttle M H et al: "Glutathione-S-transferase activates novel Alkylating Agents" Journal of Medicinal Chemistry, vol. 37,1994, pp. 1501-1507, XP002351412 ISSN: 0022-2623 Compounds 2 & 3.
Brain Tumor, Wikipedia, the free encyclopedia article, p1-5 (on-line publication, Aug. 30, 2006).

* cited by examiner

*Primary Examiner* — Yong Chu
(74) *Attorney, Agent, or Firm* — Foley & Lardner LLP

(57) ABSTRACT

Sulfonylethyl and thioethyl phosphorodiamidates, their preparation and intermediates in their preparation, formulations containing them, and their pharmaceutical use. The compounds are useful for treating cancer, alone and in combination with other anticancer therapies.

4 Claims, No Drawings

SULFONYLETHYL PHOSPHORODIAMIDATES

CROSS-REFERENCE TO RELATED APPLICATIONS

This application is a divisional of, and claims the benefit under 35 U.S.C. 120 and 121 of U.S. application Ser. No. 11/134,218, filed 20 May 2005; which in turn claims the benefit under 35 U.S.C. 119(e) of U.S. Provisional Applications Nos. 60/573,532, filed 21 May 2004, and 60/588,436, filed 16 Jul. 2004. Each of these prior applications are incorporated into this application by reference.

BACKGROUND OF THE INVENTION

1. Field of the Invention

This invention relates to sulfonylethyl and thioethyl phosphorodiamidates, formulations containing them, their pharmaceutical use, and their preparation and intermediates in their preparation.

2. Description of the Related Art

U.S. Pat. No. 5,556,942 [and PCT Publication No. WO 95/09865] discloses compounds of the formula

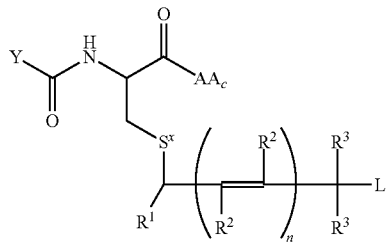

and their amides, esters, and salts, where:

L is an electron withdrawing leaving group;
$S^x$ is —S(=O)—, —S(=O)$_2$—, —S(=NH)—, —S(=O)(=NH)—, —S$^+$(C$_1$-C$_6$ alkyl)-, —Se(=O)—, —Se(=O)$_2$—, —Se(=NH)—, or —Se(=O)(=NH)—, or is —O—C(=O)—, or —HN—C(=O)—;
each $R^1$, $R^2$ and $R^3$ is independently H or a non-interfering substituent;
n is 0, 1 or 2;
Y is selected from the group consisting of

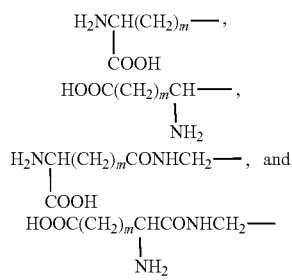

where m is 1 or 2; and
$AA_c$ is an amino acid linked through a peptide bond to the remainder of the compound.

The compounds are stated to be useful drugs for the selective treatment of target tissues which contain compatible GST isoenzymes, and simultaneously elevate the levels of GM progenitor cells in bone marrow. Disclosed embodiments for L include those that generate a drug that is cytotoxic to unwanted cells, including the phosphoramidate and phosphorodiamidate mustards.

One of the compounds has the formula

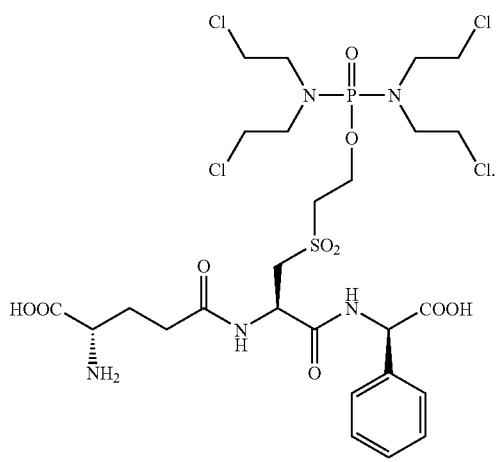

It is referred to in the patent as TER 286 and named as γ-glutamyl-α-amino-β-((2-ethyl-N,N,N,N-tetra(2'-chloro)ethylphosphoramidate)sulfonyl)propionyl-(R)-(−)-phenylglycine. This compound, later referred to as TLK286, has the CAS name L-γ-glutamyl-3-[[2-[[bis[bis(2-chloroethyl)amino]phosphinyl]oxy]ethyl]sulfonyl]-L-alanyl-2phenyl-(2R)-glycine. As the neutral compound, its proposed International Nonproprietary Name is canfosfamide; and as its hydrochloride acid addition salt, its United States Adopted Name is canfosfamide hydrochloride. Canfosfamide and its salts are anticancer compounds that are activated by the actions of GST P1-1, and by GST A1-1, to release the cytotoxic phosphorodiamidate mustard moiety.

In vitro, canfosfamide has been shown to be more potent in the M6709 human colon carcinoma cell line selected for resistance to doxorubicin and the MCF-7 human breast carcinoma cell line selected for resistance to cyclophosphamide, both of which overexpress GST P1-1, over their parental cell lines; and in murine xenografts of M7609 engineered to have high, medium, and low levels of GST P1-1, the potency of canfosfamide hydrochloride was positively correlated with the level of GST P1-1 (Morgan et al., *Cancer Res.*, 58:2568 (1998)).

Canfosfamide hydrochloride is currently being evaluated in multiple clinical trials for the treatment of ovarian, breast, non-small cell lung, and colorectal cancers. It has demonstrated significant single agent antitumor activity and improvement in survival in patients with non-small cell lung cancer and ovarian cancer, and single agent antitumor activity in colorectal and breast cancer. Evidence from in vitro cell culture and tumor biopsies indicates that canfosfamide is non-cross-resistant to platinum, paclitaxel, and doxorubicin (Rosario et al., *Mol. Pharmacol.*, 58:167 (2000)), and also to gemcitabine. Patients treated with canfosfamide hydrochloride show a very low incidence of clinically significant hematological toxicity.

PCT Publication No. WO 95/09865 also discloses intermediates that are compounds of the formula

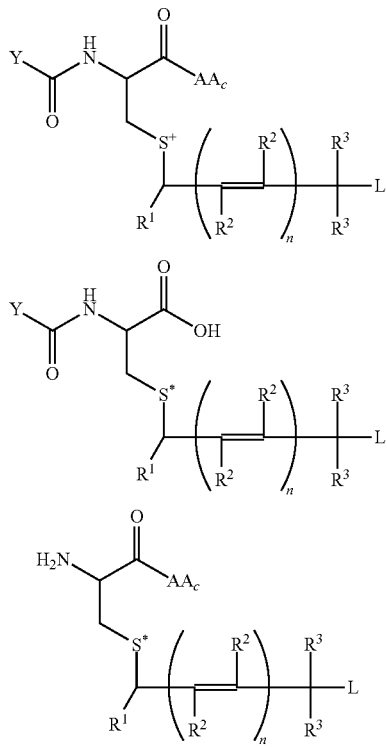

and their amides, esters, and salts, where:

L is an electron withdrawing leaving group;

$S^+$ is S or Se;

$S^*$ is —S(=O)—, —S(=O)$_2$—, —S(=NH)—, —S(=O)(=NH)—, —S$^+$(C$_1$-C$_6$ alkyl)-, —Se(=O)—, —Se(=O)$_2$—, —Se(=NH)—, or —Se(=O)(=NH)—, or is —O—C(=O)—, or —HN—C(=O)—;

each $R^1$, $R^2$ and $R^3$ is independently H or a non-interfering substituent;

n is 0, 1 or 2;

Y is selected from the group consisting of

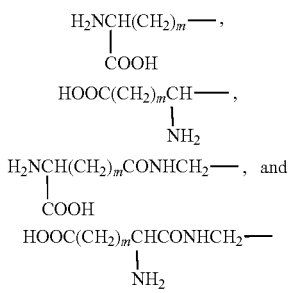

where m is 1 or 2; and $AA_c$ is an amino acid linked through a peptide bond to the remainder of the compound.

U.S. Pat. No. 6,506,739 [and PCT Publication No. WO 01/83496] discloses compounds of the formula

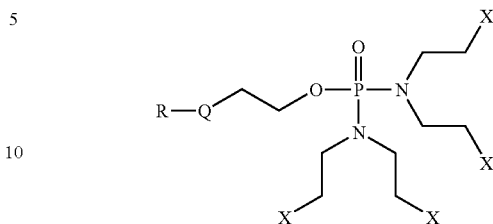

where:

X is a halogen atom;

Q is O, S, or NH; and

R is hydrogen, optionally substituted lower alkyl, optionally substituted aryl, or optionally substituted heteroaryl, or is R'CO—, R'NHCO—, R'SO$_2$—, or R'NHSO$_2$— where R' is hydrogen, optionally substituted lower alkyl, optionally substituted aryl, or optionally substituted heteroaryl; or R-Q together is chlorine;

and their salts.

The compounds are stated to be antitumor agents.

It would be desirable to develop other anticancer drugs having an efficacy and safety as good or better than canfosfamide and other compounds of U.S. Pat. No. 5,556,942.

The disclosures of U.S. Pat. Nos. 5,556,942 and 6,506,739, and the disclosures of other documents referred to in this application, are incorporated into this application by reference.

SUMMARY OF THE INVENTION

In a first aspect, this invention is compounds of formula A, B, and C:

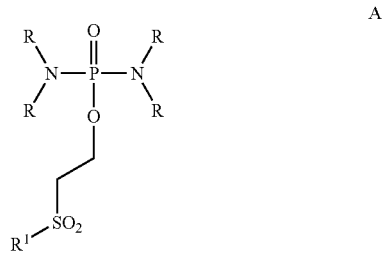

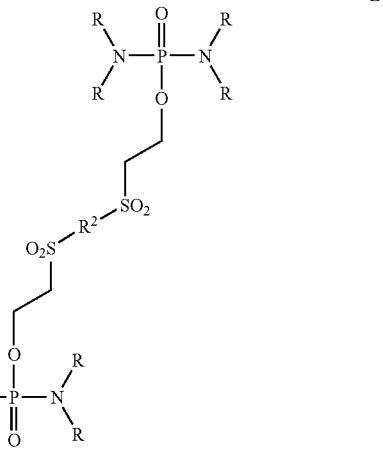

C

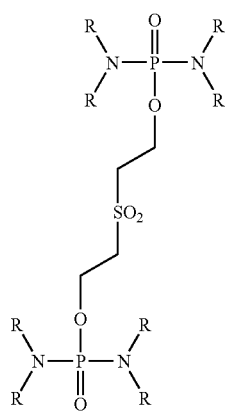

CC

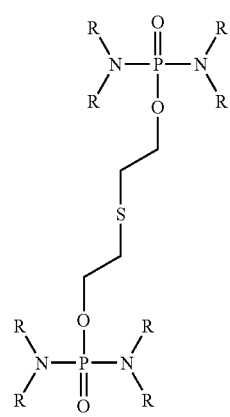

where:
each R is independently hydrogen, $C_{1-6}$ alkyl, or —$CH_2CH_2X$, where each X is independently Cl, Br, $C_{1-6}$ alkanesulfonyloxy, halo-$C_{1-6}$ alkanesulfonyloxy, or benzenesulfonyloxy optionally substituted with up to three substituents selected from halo, $C_{1-3}$ alkyl, halo-$C_{1-3}$ alkyl, $C_{1-3}$ alkyloxy, or halo-$C_{1-3}$ alkyloxy, provided that at least two R's in each phosphorodiamidate group are —$CH_2CH_2X$;

$R^1$ is optionally substituted alkyl, optionally substituted heteroalkyl, optionally substituted aryl, optionally substituted aralkyl, optionally substituted heteroaryl, or optionally substituted heteroaralkyl; and $R^2$ is optionally substituted alkanediyl, optionally substituted heteroalkanediyl, optionally substituted arenediyl, optionally substituted arenedialkyl, optionally substituted heteroarenediyl, or optionally substituted heteroarenedialkyl, and their salts.

In a second aspect, this invention is pharmaceutical compositions comprising one or more compounds of the first aspect of this invention.

In a third aspect, this invention is methods of treating cancer by the administration of a compound of the first aspect of this invention or a pharmaceutical composition of the second aspect of this invention; alone or in combination with other anticancer therapies.

In a fourth aspect, this invention is compounds of formula BB and CC:

BB

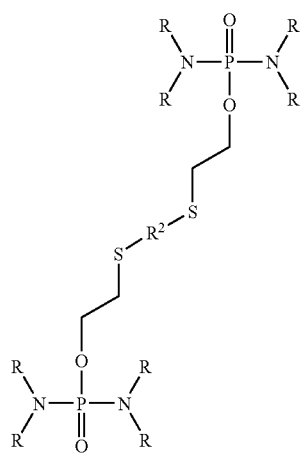

where:
each R is independently hydrogen, $C_{1-6}$ alkyl, or —$CH_2CH_2X$, where each X is independently Cl, Br, $C_{1-6}$ alkanesulfonyloxy, halo-$C_{1-6}$ alkanesulfonyloxy, or benzenesulfonyloxy optionally substituted with up to three substituents selected from halo, $C_{1-3}$ alkyl, halo-$C_{1-3}$ alkyl, $C_{1-3}$ alkyloxy, or halo-$C_{1-3}$ alkyloxy, provided that at least two R's in each phosphorodiamidate group are —$CH_2CH_2X$; and $R^2$ is optionally substituted alkanediyl, optionally substituted heteroalkanediyl, optionally substituted arenediyl, optionally substituted arenedialkyl, optionally substituted heteroarenediyl, or optionally substituted heteroarenedialkyl, and their salts.

In a fifth aspect, this invention is pharmaceutical compositions comprising one or more compounds of the fourth aspect of this invention.

In a sixth aspect, this invention is methods of treating cancer by the administration of a compound of the fourth aspect of this invention or a pharmaceutical composition of the fifth aspect of this invention; alone or in combination with other anticancer therapies.

In a seventh aspect, this invention is methods of preparing compounds of the first and fourth aspects of this invention. Compounds of the first aspect of this invention are conveniently prepared from compounds of the fourth aspect of this invention.

DETAILED DESCRIPTION OF THE INVENTION

Definitions

"Alkyl" means a monovalent group derived from a saturated or unsaturated (but not aromatically unsaturated) $C_1$-$C_{10}$ hydrocarbon that may be linear, branched, or cyclic by removal of one hydrogen atom from a carbon atom. Examples are methyl, ethyl, propyl, 1-propenyl, isopropyl, butyl, isobutyl, sec-butyl, tert-butyl, pentyl, hexyl, cyclopentyl, cyclopenten-1-yl, cyclopropylmethyl, cyclohexyl, and cyclohexylmethyl. Saturated alkyls (including cycloalkyls) and $C_1$-$C_6$ alkyls are exemplary. Note that the definition of "alkyl" in this application is broader than the conventional definition and includes groups more commonly referred to as "cycloalkyl", "cycloalkylalkyl", "alkenyl", and "alkynyl". "Alkanediyl" means a divalent group derived from an "alkyl" (as that term is defined here) by removal of a second hydrogen atom from the same carbon atom or another carbon atom, preferably from another carbon atom. Examples are 1,2-ethanediyl, but-2-en-1,4-diyl, 1,5-pentanediyl, and 1,4-cyclohexanediyl.

A "substituted alkyl" is an alkyl substituted with up to three halogen atoms and/or up to three substituents selected from —CN, —NO$_2$, —OR, —SR, —COR, —OC(O)R, —C(O)OR, —NR$_2$, —NR$_3^+$X$^-$, —PR$_2$, —PR$_3^+$X$^-$, —SO$_2$OR, —OSO$_2$R, —SO$_2$NR$_2$, —NRSO$_2$R, —CONR$_2$, —NRCOR, and —NRC(O)OR, where each R is, independently, hydrogen, optionally R'-substituted alkyl, optionally R'-substituted heteroalkyl, optionally R'-substituted aryl, optionally R'-substituted heteroaryl, optionally R'-substituted aralkyl, or optionally R'-substituted heteroaralkyl and each R' is, independently, 1 to 3 substituents selected from halo, —CN, —NO$_2$, —OH, C$_{1-3}$ alkyl, C$_{1-3}$ alkyloxy, —SH, —NH$_2$, or —C(O)Oalkyl (preferably, 1 to 3 substituents selected from halo, —CN, —NO$_2$, —OH, C$_{1-3}$ alkyl, C$_{1-3}$ alkyloxy, —SH, or —NH$_2$), or two R groups form a 4- or 5-member optionally R'-substituted alkanediyl or optionally R'-substituted heteroalkanediyl, and X is a halogen. Thus, for example, substituted alkyl groups include such groups as trifluoromethyl, 3-chloropropyl, and 2-morpholinoethyl. Substituted alkyl groups also include the residues (i.e. all except the thiol) of thiol-amino acids such as cysteine, homocysteine, and penicillamine, and their esters and amides formed by reaction at the carboxy group and amides or sulfonamides formed by reaction at the amine group, such as their N-protected forms and esters, where one substituent is —COOR and another substituent is —NH$_2$ or —NRC(O)OR. "Substituted alkanediyl" means alkanediyl substituted in the manner described above for an alkyl. Compounds of this invention also include compounds where any non-aromatic amine having 1 or 2 hydrogen atoms present is protected by an amine-protecting group of the formula R*OC(O)— such as tert-butoxycarbonyl, benzyloxycarbonyl, fluorenylmethoxycarbonyl, and other similar conventional carbamate-forming protecting groups. The term "substituted alkyl" specifically excludes dipeptides and higher peptides based on cysteine (i.e. where the "substituted alkyl" is bonded to the sulfonylethyl phosphorodiamidate portion of the molecule through the cysteine sulfur atom) and their esters, amides, and ester/amides. "Elaborated" refers to the conversion of a reactive substituent to another typically more complex substituent, such as the conversion of an amine to an amide or sulfonamide, a carboxy group to an ester or amide, a hydroxy to an ester, and conversion of an amide or sulfonamide with one or more hydrogen atoms on the nitrogen to one where one or more of those hydrogen atoms is replaced by an optionally substituted alkyl, heteroalkyl, aryl, heteroaryl, aralkyl, or heteroaralkyl group. "Protected" has its conventional meaning in organic synthesis, namely the temporary conversion of a reactive substituent to a substituent that is non-reactive under the conditions of the reaction(s) proposed to be carried out; such as the protection of an amine as a carbamate as mentioned above.

"Heteroalkyl" means alkyl in which 1 to 3 of the carbon atoms are replaced by O, S, or NR (where R is H or C$_{1-3}$ alkyl optionally substituted with halogen or hydroxy), including linear groups such as 3-oxapentyl; monocyclic rings containing 5 or 6 ring atoms such as 2-tetrahydrofuranyl, 2-pyrrolidinyl, 3-piperidinyl, 2-piperazinyl, 4-methyl-1-piperazinyl, 4-dihydropyranyl, and 3-morpholinyl; and groups such as tetrahydrofuran-2-ylmethyl and piperidin-3-ylethyl. "Heteroalkanediyl" means a divalent group derived from a heteroalkyl by removal of a second hydrogen atom, such as 3-oxapentane-1,5-diyl. Heteroalkyl and heteroalkanediyl groups also include those where a ring nitrogen is oxidized to form an N-oxide. A "cycloamino" group is a cyclic heteroalkyl of 5 to 7 ring atoms containing a nitrogen ring atom by which the group is bonded to the remainder of the molecule of which it forms a part and optionally containing a further ring heteroatom selected from O, S, and NR (where R is H or C$_{1-3}$ alkyl optionally substituted with halogen, hydroxy, or 1 or 2 phenyl groups). 4-Methyl-1-piperazinyl, 4-(2-hydroxyethyl)-1-piperazinyl, 4-(diphenylmethyl)-1-piperazinyl, and 4-morpholinyl are examples of cycloamino groups. Compounds of this invention also include compounds where any —NR$_2$ group present is replaced by a cycloamino group.

"Substituted heteroalkyl" and "substituted hereteroalkanediyl" mean heteroalkyl and heteroalkanediyl substituted in the manner described above for substituted alkyl.

"Aryl" means a monovalent group derived from an aromatic hydrocarbon containing 6 to 14 ring carbon atoms by removal of one hydrogen atom from a carbon atom, which is monocyclic (e.g., phenyl), condensed polycyclic, for example, condensed bicyclic (e.g., naphthyl), or linked polycyclic, for example, linked bicyclic (e.g., biphenylyl). "Arenediyl" means a divalent group derived from an aryl by removal of a second hydrogen atom from a carbon atom, such as 1,4-benzenediyl, 1,5-naphthalenediyl, and biphenyl-4,4'-diyl. A preferred aryl is phenyl, and a preferred arenediyl is benzenediyl (any isomer).

"Substituted aryl" means aryl substituted with up to three substituents selected from halo, —CN, —NO$_2$, —OR, optionally halo-substituted C$_{1-3}$ alkyl, optionally halo-substituted C$_{1-3}$ alkyloxy, —SR, —COR, —OC(O)R, —C(O)OR, —NR$_2$, —NR$_3^+$X$^-$, —PR$_2$, —PR$_3^+$X$^-$, —SO$_2$OR, —OSO$_2$R, —SO$_2$NR$_2$, —NRSO$_2$R, —CONR$_2$, —NRCOR, and —NRC(O)OR, where each R is hydrogen, optionally R'-substituted alkyl, optionally R'-substituted heteroalkyl, optionally R'-substituted aryl, optionally R'-substituted heteroaryl, optionally R'-substituted aralkyl, or optionally R'-substituted heteroaralkyl (preferably, hydrogen or optionally R'-substituted alkyl) and each R' is, independently, 1 to 3 substituents selected from halo, —CN, —NO$_2$, —OH, C$_{1-3}$ alkyl, C$_{1-3}$ alkyloxy, —SH, —NH$_2$, or —C(O)Oalkyl (preferably, halo, —CN, —NO$_2$, —OH, C$_{1-3}$ alkyl, C$_{1-3}$ alkyloxy, —SH, or —NH$_2$), or two R groups form a 4- or 5-member optionally R'-substituted alkanediyl or optionally R'-substituted heteroalkanediyl, and X is a halogen. Two adjacent substituents may also form a methylenedioxy or ethylenedioxy group. Substituted aryl groups include aryl groups substituted with up to three substituents selected from the group consisting of halo, —CN, —NO$_2$, —OH, optionally halo-substituted C$_{1-3}$ alkyl, optionally halo-substituted C$_{1-3}$ alkyloxy, —SH, and —NH$_2$, for example, phenyl substituted in this way. "Substituted arenediyl" means arenediyl substituted in the manner described above for an aryl. Preferred substituted aryls are substituted phenyls.

"Aralkyl" means alkyl substituted with aryl, such as benzyl and phenethyl. A preferred aralkyl is benzyl. "Arenedialkyl" means two alkyls jointly substituted with arenediyl, such as benzene-1,4-dimethyl. A preferred arenedialkyl is benzenedimethyl (any isomer).

"Substituted aralkyl" means aralkyl in which one or both of the aryl and the alkyl are substituted in the manner described above for substituted aryl and substituted alkyl; and "substituted arenedialkyl" means arenedialkyl in which one or more of the arenediyl and the two alkyls are substituted in the manner described above for substituted arenediyl and substituted alkyl. The preferred substituted aralkyls are substituted benzyls; and preferred substituted arenedialkyls are substituted benzenedimethyls.

"Halogen" or "halo" means F, Cl, or Br.

"Heteroaryl" means aryl in which 1 to 4 (preferably 1 to 3) of the ring carbon atoms are replaced by O, S, N, or NR (where R is H or $C_{1-3}$ alkyl), preferably O, S, or NR, including monocyclic groups containing 5 or 6 ring atoms such as furanyl, thienyl, pyrrolyl, oxazolyl, imidazolyl, pyridinyl, pyrazinyl, pyridazinyl, pyrimidinyl, and the like, and bicyclic groups such as benzothiazolyl, purinyl, and benzimidazolyl. Monocyclic rings are preferred. "Heteroarenediyl" means a divalent group derived from a heteroaryl by removal of a second hydrogen atom from a carbon atom. Heteroaryl and heteroarenediyl groups also include those where a ring nitrogen is oxidized to form an N-oxide.

"Substituted heteroaryl" and "substituted heteroarenediyl" mean heteroaryl and heteroarenediyl substituted in the manner described above for substituted aryl.

"Heteroaralkyl" means alkyl substituted with heteroaryl, such as 2-thienylmethyl. "Heteroarenedialkyl" means two alkyls substituted jointly with heteroarenediyl, such as 2,5-furanyldiethyl.

"Substituted heteroaralkyl" and "substituted heteroarenedialkyl" mean heteroaralkyl and heteroarenedialkyl substituted in the manner described above for substituted alkyl and substituted arenedialkyl.

"Salts" are described in the section entitled "Compounds of this invention".

A "therapeutically effective amount" means that amount which, when administered to a human for treating a cancer, is sufficient to effect treatment for the cancer. "Treating" or "treatment" of a cancer in a human includes one or more of:
(1) limiting/inhibiting growth of the cancer, i.e., limiting/arresting its development,
(2) reducing/preventing spread of the cancer, i.e. reducing/preventing metastases,
(3) relieving the cancer, i.e., causing regression of the cancer,
(4) reducing/preventing recurrence of the cancer, and
(5) palliating symptoms of the cancer.

"Combination therapy" means the administration of a compound of the first or fourth aspects of this invention and another anticancer therapy during the course of cancer chemotherapy. Such combination therapy may involve the administration of the compound of the first or fourth aspect of this invention before, during, and/or after the administration of the another anticancer therapy. The administration of the compound of the first or fourth aspect of this invention may be separated in time from the administration of the another anticancer therapy by up to several weeks, and may precede it or follow it, but more commonly the administration of the compound of the first or fourth aspect of this invention will accompany at least one aspect of the another anticancer therapy (such as the administration of one dose of a chemotherapeutic agent, molecular targeted therapy agent, biologic therapy agent, or radiation therapy) within up to 48 hours, and most commonly within less than 24 hours.

"Another anticancer therapy" is an anticancer therapy that is not a treatment with a compound of the first or fourth aspect of this invention. Such "another anticancer therapies" include chemotherapy; molecular targeted therapy; biologic therapy; and radiotherapy. These therapies are those used as monotherapy or in combination therapy.

Chemotherapeutic agents include:
alkylating agents, including:
alkyl sulfonates such as busulfan,
ethyleneimine derivatives such as thiotepa,
nitrogen mustards such as chlorambucil, cyclophosphamide, estramustine, ifosfamide, mechlorethamine, melphalan, and uramustine,
nitrosoureas such as carmustine, lomustine, and streptozocin,
triazenes such as dacarbazine, procarbazine, and temozolamide, and
platinum compounds such as cisplatin, carboplatin, oxaliplatin, satraplatin, and picoplatin; antimetabolites, including:
antifolates such as methotrexate, permetrexed, raltitrexed, and trimetrexate,
purine analogs such as cladribine, chlorodeoxyadenosine, clofarabine, fludarabine, mercaptopurine, pentostatin, and thioguanine,
pyrimidine analogs such as azacitidine, capecitabine, cytarabine, edatrexate, floxuridine, fluorouracil, gemcitabine, and troxacitabine;
natural products, including:
antitumor antibiotics such as bleomycin, dactinomycin, mithramycin, mitomycin, mitoxantrone, porfiromycin, and anthracyclines such as daunorubicin (including liposomal daunorubicin), doxorubicin (including liposomal doxorubicin), epirubicin, idarubicin, and valrubicin,
enzymes such as L-asparaginase and PEG-L-asparaginase,
microtubule polymer stabilizers such as the taxanes paclitaxel and docetaxel,
mitotic inhibitors such as the vinca alkaloids vinblastine, vincristine, vindesine, and vinorelbine,
topisomerase I inhibitors such as the camptothecins irinotecan and topotecan, and
topoisomerase II inhibitors such as amsacrine, etoposide, and teniposide;
hormones and hormone antagonists, including:
androgens such as fluoxymesterone and testolactone,
antiandrogens such as bicalutamide, cyproterone, flutamide, and nilutamide,
aromatase inhibitors such as aminoglutethimide, anastrozole, exemestane, formestane, and letrozole,
corticosteroids such as dexamethasone and prednisone,
estrogens such as diethylstilbestrol,
antiestrogens such as fulvestrant, raloxifene, tamoxifen, and toremifine,
LHRH agonists and antagonists such as buserelin, goserelin, leuprolide, and triptorelin,
progestins such as medroxyprogesterone acetate and megestrol acetate, and
thyroid hormones such as levothyroxine and liothyronine; and
miscellaneous agents, including altretamine, arsenic trioxide, gallium nitrate, hydroxyurea, levamisole, mitotane, octreotide, procarbazine, suramin, thalidomide, lenalidomide, photodynamic compounds such as methoxsalen and sodium porfimer, and proteasome inhibitors such as bortezomib.

Molecular targeted therapy agents include:
functional therapeutic agents, including:
gene therapy agents,
antisense therapy agents,
tyrosine kinase inhibitors such as erlotinib hydrochloride, gefitinib, imatinib mesylate, and semaxanib, and
gene expression modulators such as the retinoids and rexinoids, e.g. adapalene, bexarotene, trans-retinoic acid, 9-cis-retinoic acid, and N-(4-hydroxyphenyl)retinamide;
phenotype-directed therapy agents, including:
monoclonal antibodies such as alemtuzumab, bevacizumab, cetuximab, ibritumomab tiuxetan, rituximab, and trastuzumab;
immunotoxins such as gemtuzumab ozogamicin,
radioimmunoconjugates such as $^{131}$I-tositumomab, and
cancer vaccines.

Biologic therapy agents include:

interferons such as interferon-$\alpha_{2a}$ and interferon-$\alpha_{2b}$, and interleukins such as aldesleukin, denileukin diftitox, and oprelvekin.

In addition to these agents intended to act against cancer cells, anticancer therapies include the use of protective or adjunctive agents, including:

cytoprotective agents such as amifostine, dexrazoxane, and mesna, phosphonates such as pamidronate and zoledronic acid, and stimulating factors such as epoetin, darbeopetin, filgrastim, PEG-filgrastim, and sargramostim.

Combination cancer therapy regimens with which the compounds of the first aspect of this invention may be combined include all regimens involving the use of two or more of the anticancer therapies (anticancer agents) such as those mentioned in paragraphs [0038] to [0040] above and/or radiotherapy, optionally including protective and adjunctive agents such as those mentioned in paragraph [0041] above; and the compound of the first or second aspect of this invention can be added to existing anticancer regimens known for the treatment of various cancers, such as the regimens mentioned in such books as *Cancer Chemotherapy and Biotherapy: Principles and Practice,* 3rd ed. (2001), Chabner and Longo, eds., and *Handbook of Cancer Chemotherapy,* 6th ed. (2003), Skeel, ed., both from Lippincott Williams & Wilkins, Philadelphia, Pa., U.S.A.; and regimens for anticancer therapies, especially chemotherapies, may be found on Web sites such as those maintained by the National Cancer Institute (www.cancer.gov), the American Society for Clinical Oncology (www.asco.org), and the National Comprehensive Cancer Network (www.nccn.org).

Many combination chemotherapeutic regimens are known to the art, such as combinations of platinum compounds and taxanes, e.g. carboplatin/paclitaxel, capecitabine/docetaxel, the "Cooper regimen", fluorouracil-levamisole, fluorouracil-leucovorin, methotrexate-leucovorin, and those known by the acronyms ABDIC, ABVD, AC, ADIC, AI, BACOD, BACOP, BVCPP, CABO, CAD, CAE, CAF, CAP, CD, CEC, CF, CHOP, CHOP+rituximab, CIC, CMF, CMFP, CyADIC, CyVADIC, DAC, DVD, FAC, FAC-S, FAM-S, FOLFOX-4, FOLFOX-6, M-BACOD, MACOB-B, MAID, MOPP, MVAC, PCV, T-5, VAC, VAD, VAPA, VAP-Cyclo, VAP-II, VBM, VBMCP, VIP, VP, and the like.

Combinations of chemotherapies and molecular targeted therapies, biologic therapies, and radiation therapies are also well known to the art; including therapies such as trastuzumab+paclitaxel, alone or in further combination with carboplatin, for certain breast cancers, and many other such regimens for other cancers; and the "Dublin regimen" and "Michigan regimen", both for esophageal cancer, and many other such regimens for other cancers.

"Comprising" or "containing" and their grammatical variants are words of inclusion and not of limitation and mean to specify the presence of stated components, groups, steps, and the like but not to exclude the presence or addition of other components, groups, steps, and the like. Thus "comprising" does not mean "consisting of", "consisting substantially of", or "consisting only of"; and, for example, a formulation "comprising" a compound must contain that compound but may also may contain other active ingredients and/or excipients.

Compounds of This Invention

In a first aspect, this invention is sulfonylethyl phosphorodiamidates, compounds of formula A, B, and C:

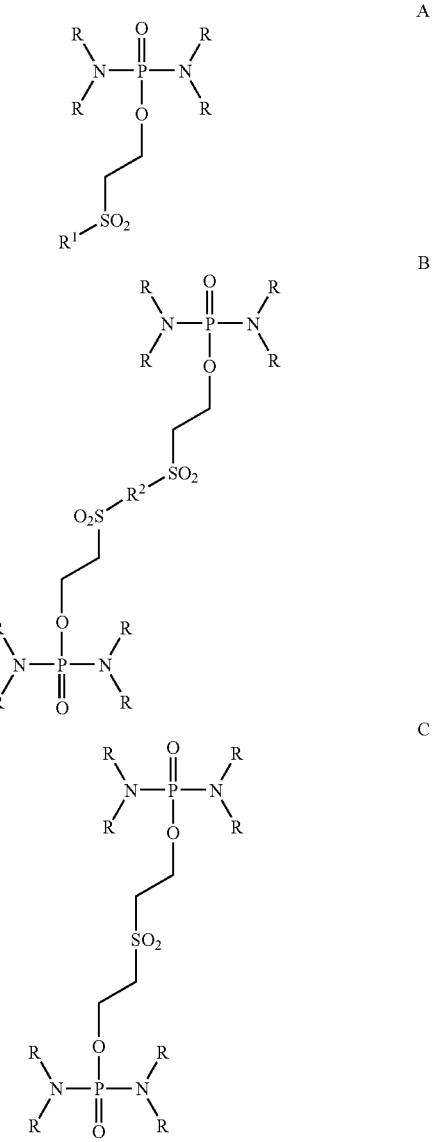

where:

each R is independently hydrogen, $C_{1-6}$ alkyl, or —$CH_2CH_2X$, where each X is independently Cl, Br, $C_{1-6}$ alkanesulfonyloxy, halo-$C_{1-6}$ alkanesulfonyloxy, or benzenesulfonyloxy optionally substituted with up to three substituents selected from halo, $C_{1-3}$ alkyl, halo-$C_{1-3}$ alkyl, $C_{1-3}$ alkyloxy, or halo-$C_{1-3}$ alkyloxy, provided that at least two R's in each phosphorodiamidate group are —$CH_2CH_2X$;

$R^1$ is optionally substituted alkyl, optionally substituted heteroalkyl, optionally substituted aryl, optionally substituted aralkyl, optionally substituted heteroaryl, or optionally substituted heteroaralkyl; and $R^2$ is optionally substituted alkanediyl, optionally substituted heteroalkanediyl, optionally substituted arenediyl, optionally substituted arenedialkyl, optionally substituted heteroarenediyl, or optionally substituted heteroarenedialkyl, and their salts.

In a fourth aspect, this invention is thioethyl phosphorodiamidates, compounds of formula BB and CC:

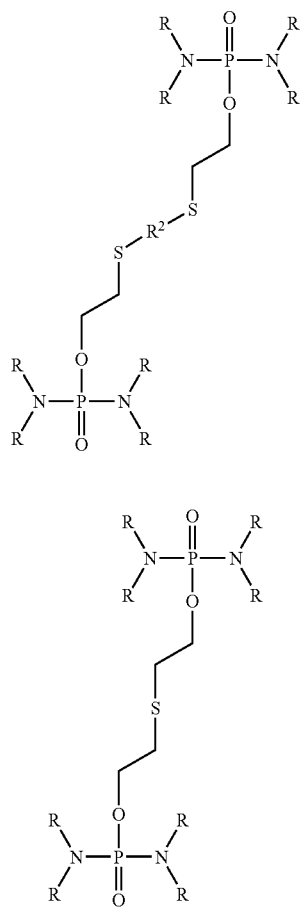

where:
each R is independently hydrogen, $C_{1-6}$ alkyl, or —$CH_2CH_2X$, where each X is independently Cl, Br, $C_{1-6}$ alkanesulfonyloxy, halo-$C_{1-6}$ alkanesulfonyloxy, or benzenesulfonyloxy optionally substituted with up to three substituents selected from halo, $C_{1-3}$ alkyl, halo-$C_{1-3}$ alkyl, $C_{1-3}$ alkyloxy, or halo-$C_{1-3}$ alkyloxy, provided that at least two R's in each phosphorodiamidate group are —$CH_2CH_2X$; and $R^2$ is optionally substituted alkanediyl, optionally substituted heteroalkanediyl, optionally substituted arenediyl, optionally substituted arenedialkyl, optionally substituted heteroarenediyl, or optionally substituted heteroarenedialkyl, and their salts.

Salts (for example, pharmaceutically acceptable salts) of the compounds of formulae A, B, C, BB, and CC are included in the present invention and are useful in the compositions, methods, and uses described in this application (see Berge et al., J. Pharm. Sci., 66:1 (1971) for a nonexclusive list of pharmaceutically acceptable salts).

These salts include salts that may be formed when acidic protons present are capable of reacting with inorganic or organic bases. Typically the parent compound is treated with an excess of an alkaline reagent, such as hydroxide, carbonate or alkoxide, containing an appropriate cation. Cations such as $Na^+$, $K^+$, $Ca^{2+}$, $Mg^{2+}$ and $NH_4^+$ are examples of cations present in pharmaceutically acceptable salts. Suitable inorganic bases, therefore, include calcium hydroxide, potassium hydroxide, sodium carbonate and sodium hydroxide. Salts may also be prepared using organic bases, such as salts of primary, secondary and tertiary amines, substituted amines including naturally-occurring substituted amines, and cyclic amines including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, and the like.

If a compound of the first or fourth aspects of this invention contains a basic group, such as an amino or phosphino group, it may be prepared as an acid addition salt. Acid addition salts of the compounds are prepared in a standard manner in a suitable solvent from the parent compound and an excess of an acid, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, 4-toluenesulfonic acid, hexanoic acid, heptanoic acid, cyclopentanepropionic acid, lactic acid, 2-(4-hydroxybenzoyl)benzoic acid, 1,2-ethanedisulfonic acid, 2-hydroxyethanesulfonic acid, benzenesulfonic acid, 4-chlorobenzenesulfonic acid, 2-naphthalenesulfonic acid, camphorsulfonic acid, 4-methylbicyclo[2.2.2.]oct-2-ene-1-carboxylic acid, glucoheptonic acid, gluconic acid, 4,4'-methylenebis(3-hydroxy-2-naphthoic)acid, 3-phenylpropionic acid, trimethylacetic acid, tert-butylacetic acid, laurylsulfuric acid, glucuronic acid, glutamic acid, 3-hydroxy-2-naphthoic acid, stearic acid, muconic acid and the like.

Certain of the compounds may form inner salts or zwitterions.

Certain compounds of formula A, B, and BB of the invention may contain one or more chiral centers (for example, those based on amino acids). In such cases, all individual stereoisomers and racemic and non-racemic mixtures of the stereoisomers of the compounds (and their salts) are included in this invention. Typically the stereochemistry of the compounds of this invention will be dictated by the stereochemistry of the thiols of formula $A^1$ and $B^1$, and methods for the isolation of individual stereoisomers of such thiols, for example, the resolution of thiol-amino acids such as cysteine, are well known to a person of ordinary skill in the art and are therefore not described here. In many instances, such as with cysteine and penicillamine, individual stereoisomers and racemic mixtures of stereoisomers are commercially available; and other thiols such as dithiothreitol and dithioerythritol exist as individual stereoisomers.

The compounds are named in this application semi-systematically based on the CAS name of canfosfamide (i.e. with the thioethyl or sulfonylethyl phosphorodiamidate portion of the molecule named as a substituent on the remainder of the molecule). Thus, the compounds 70A, 128A, 23B, and 1C below:

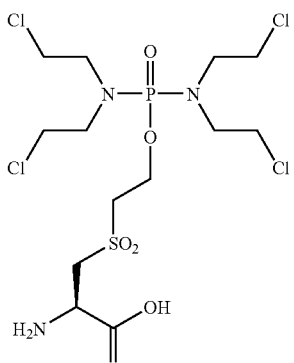

70A

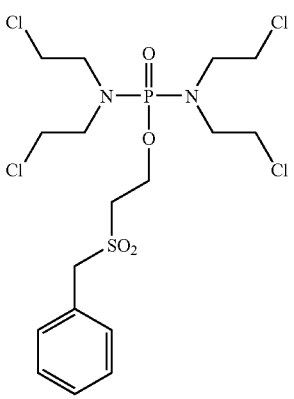

128A

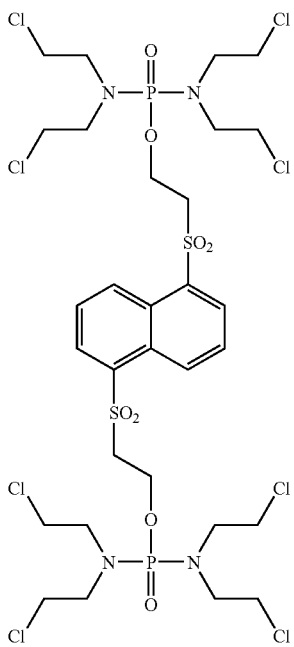

23B

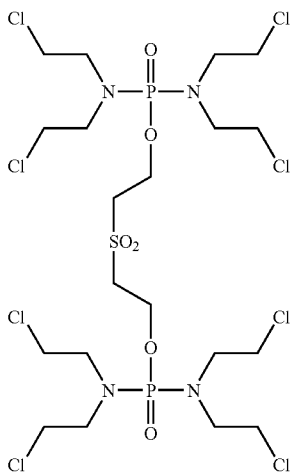

1C are named 3-[[2-[[bis[bis(2-chloroethyl)amino]phosphinyl]oxy]ethyl]sulfonyl]-L-alanine, α-[[2-[[bis[bis(2-chloroethyl)amino]phosphinyl]oxy]ethyl]sulfonyl]toluene, 1,5-di[[2-[[bis[bis(2-chloroethyl)amino]phosphinyl]oxy]ethyl]sulfonyl]naphthalene, and di[2-[[bis[bis(2-chloroethyl)amino]phosphinyl]oxy]ethyl]sulfone, respectively.

Compounds of this invention include those compounds of formulae A, B, C, BB, and CC where one or more of the following is true:

1. each R is —$CH_2CH_2X$;
2. each X is Cl, Br, methanesulfonyloxy, trifluoromethanesulfonyloxy, benzenesulfonyloxy, or 4-toluenesulfonyloxy; especially where X is Cl or Br; particularly Cl;
3. the compound is a compound of formula A;
4. $R^1$ is substituted with one or more groups that enhance the solubility of the compound over a compound that is not so substituted, for example, hydroxy, carboxy, sulfo, amino, quaternary ammonium, phosphino, and quaternary phosphonium;
5. $R^1$ is optionally substituted alkyl, or optionally substituted aryl, or optionally substituted aralkyl; and
6. $R^1$ is the residue of an optionally protected thiol-amino acid, or an elaborated thiol-amino acid such as an amide or ester formed by reaction at the carboxy group and/or amide or sulfonamide formed by reaction at the amine group, preferably the residue of a thiol-amino acid;
7. $R^1$ is the residue of 2-mercaptoacetic acid or 3-mercaptopropionic acid, or an elaborated acid such as an amide or ester formed by reaction at the carboxy group, particularly the residue of an optionally elaborated 2-mercaptoacetamide;
8. the compound is a compound of formula B;
9. $R^2$ is substituted with one or more groups that enhance the solubility of the compound over a compound that is not so substituted, for example, hydroxy, carboxy, sulfo, amino, quaternary ammonium, phosphino, and quaternary phosphonium; or
10. the compound is a compound of formula C.

Compounds of this invention include each of the compounds described in the specification and claims of this application as filed, including in the Examples below, especially compounds 5A, 13A, 15A, 23A, 70A, 128A, 171A, 172A, and 180A, and their salts. Compositions and methods of this invention include compositions and methods where the compound is one of those mentioned in the preceding sentence.

Preparation of the Compounds

Sulfonylethyl phosphorodiamidates of formula A, B, and C may conveniently be prepared by oxidation of the corresponding thioethyl phosphorodiamidates of formulae AA, BB, and CC (with any reactive moiety in $R^1$ or $R^2$ protected against oxidation if necessary), as follows:

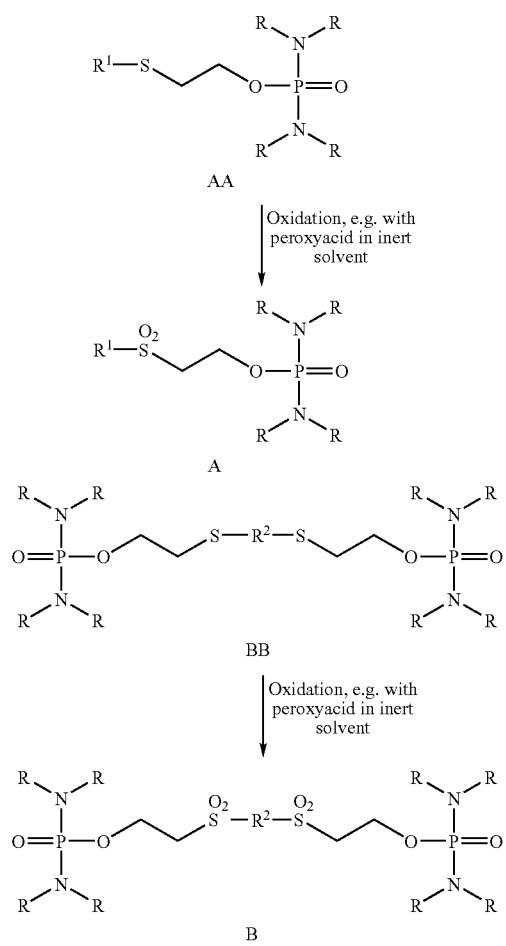

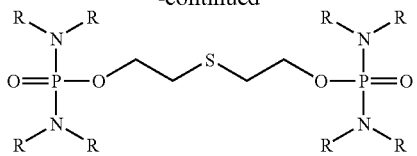

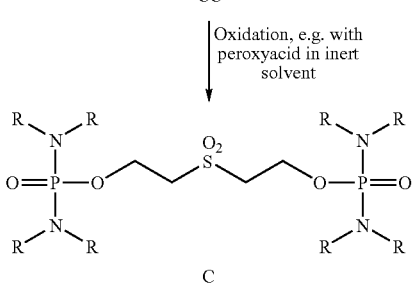

This oxidation may be performed by any of the methods own in the art for the oxidation of thioethers to sulfones, such as the use of peracids (peroxycarboxylic acids), persulfates, perborates, peroxides, ozone, iodosyl reagents, halogens, and the like. If the compound of formula AA or BB contains a reactive moiety in $R^1$ or $R^2$, such as an amine group, that reactive moiety may be protected before the oxidation and the resulting protected compound of formula A or B deprotected if desired to yield the final compound (though the protected compounds are also among compounds of this invention). Such protection and deprotection is seen in Synthetic Example 2, for example. Where a peracid is used, a typical procedure involves dissolving the compound of formula AA, BB, or CC in a solvent such as acetic acid or isopropyl acetate at reduced temperature, followed by the addition of the peracid (e.g. peracetic acid) in excess.

After oxidation and optional deprotection, the compounds of formula A and formula B may be elaborated by synthetic methods known per se, as discussed later in this application.

The thioethyl phosphorodiamidates of formula AA and BB may conveniently be prepared by one of to methods:

(1) reaction of the corresponding thiols of formula $A^1$ and $B^1$ with a 2-$X^1$-ethyl phosphorodiamidate (where $X^1$ is Cl, Br, or an alkane- or arenesulfonyloxy group such as methanesulfonyloxy, benzenesulfonyloxy, or 4-toluenesulfonyloxy), as follows:

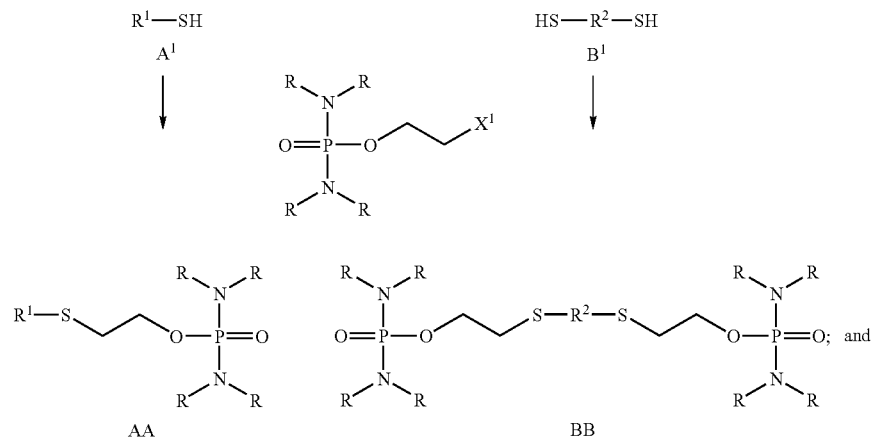

(2) (a) reaction of the thiols of formula $A^1$ and $B^1$ with a 2-$X^1$-ethanol (where $X^1$ is Cl, Br, $C_{1-6}$ alkanesulfonyloxy, halo-$C_{1-6}$ alkanesulfonyloxy, or benzenesulfonyloxy optionally substituted with up to three substituents selected from halo, $C_{1-3}$ alkyl, halo-$C_{1-3}$ alkyl, $C_{1-3}$ alkyloxy, or halo-$C_{1-3}$ alkyloxy) to first form the corresponding 2-hydroxyethyl thiols of formula $A^2$ and $B^2$, followed by (b) reaction of the 2-hydroxyethyl thiols with a phosphorodiamidyl halide or alkane- or arenesulfonate ($X^2$ is Cl, Br, $C_{1-6}$ alkanesulfonyloxy, halo-$C_{1-6}$ alkanesulfonyloxy, or benzenesulfonyloxy optionally substituted with up to three substituents selected from halo, $C_{1-3}$ alkyl, halo-$C_{1-3}$ alkyl, $C_{1-3}$ alkyloxy, or halo-$C_{1-3}$ alkyloxy), as follows:

After optional deprotection, the compounds of formula AA and formula BB may be elaborated by synthetic methods known per se, as discussed later in this application.

The compounds of formula CC are conveniently prepared by a two-step synthesis, in which 2,2'-thiodiethanol is reacted with a sub-stoichiometric amount of a phosphorodiamidyl halide or alkane- or arenesulfonate in an aprotic solvent in the presence of a base such as an alkoxide to give the monophosphorodiamidate ester, and that ester is then reacted with an excess of the phosphorodiamidyl halide or alkane- or arenesulfonate, again in an aprotic solvent in the presence of a base such as an alkoxide, to give the bis-phosphorodiamidate ester, as follows:

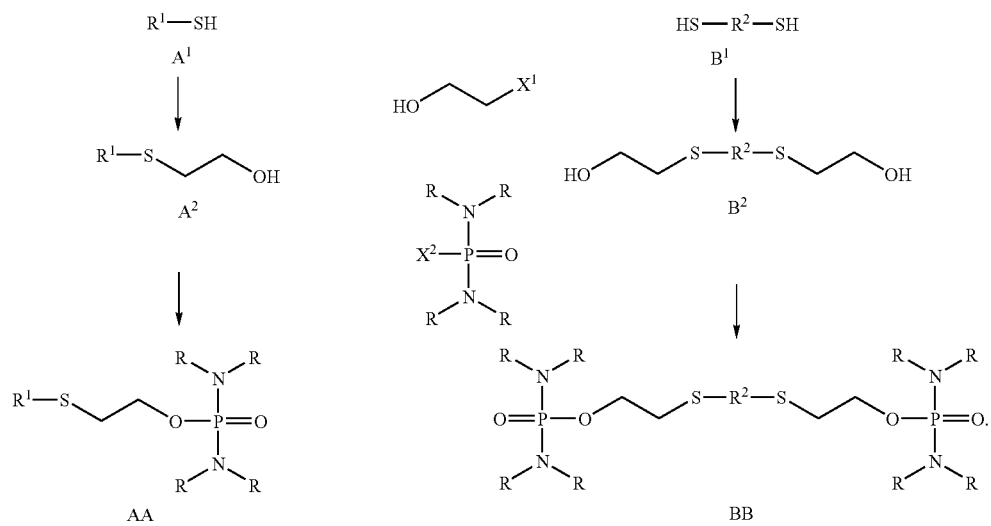

The direct conversion of thiols of formula $A^1$ and $B^1$ to the thioethyl phosphorodiamidates of formula AA and BB may be performed by any of the methods known in the art for alkylation of thiols. A typical procedure involves dissolving the thiol of formula $A^1$ or $B^1$ in a polar solvent such as water, an alcohol, dimethylformamide, or tetrahydrofuran, then treating it with a base such as a hydroxide, alkoxide, fluoride, or tertiary amine or amide base to form the thiolate anion, followed by adding the phosphorodiamidate. Thiolate displacement of the leaving group $X^1$ of the 2-$X^1$-ethyl phosphorodiamidate gives the compounds of formula AA and BB.

Alternatively, the thiols of formula $A^1$ and $B^1$ may be treated with ethanol 2-substituted with Cl, Br, $C_{1-6}$ alkanesulfonyloxy, halo-$C_{1-6}$ alkanesulfonyloxy, or benzenesulfonyloxy optionally substituted with up to three substituents selected from halo, $C_{1-3}$ alkyl, halo-$C_{1-3}$ alkyl, $C_{1-3}$ alkyloxy, or halo-$C_{1-3}$ alkyloxy, e.g. 2-chloroethanol, under the conditions of the previous paragraph to give the 2-hydroxyethylthiol compounds of formula $A^2$ and $B^2$, which may then be converted to the compounds of formula AA and BB, typically by reacting the compounds of formula $A^2$ and $B^2$ with a phosphorodiamidyl halide or alkane- or arenesulfonate in an aprotic solvent such as tetrahydrofuran, toluene, or dichloromethane in the presence of an base such as an alkoxide or tertiary amine.

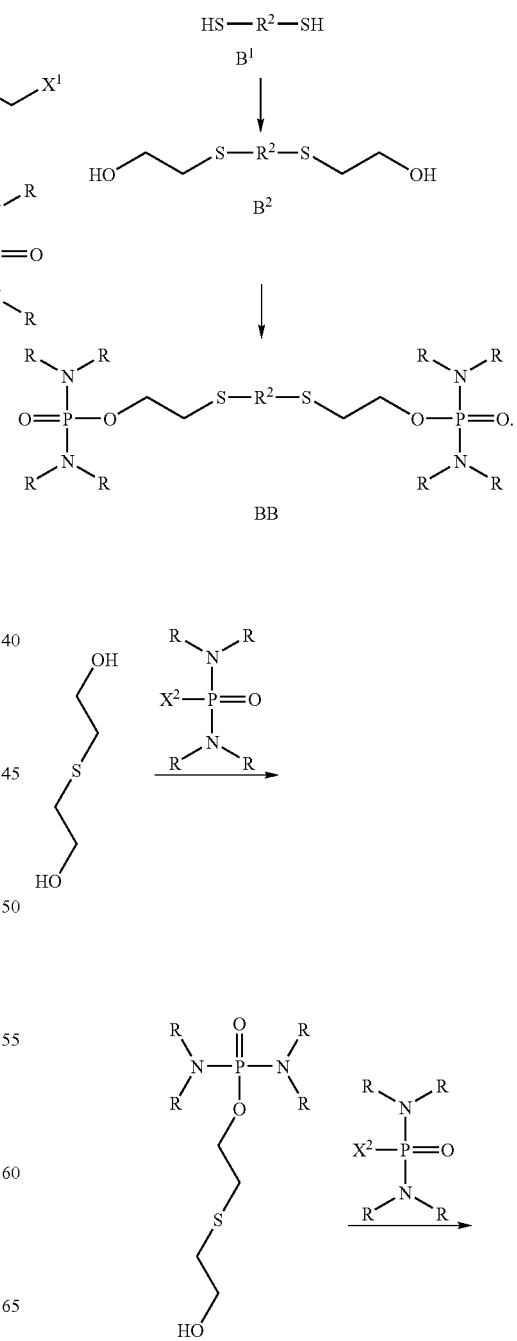

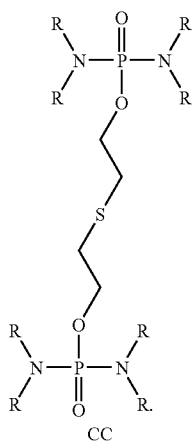

CC

Pharmaceutical Compositions and Administration

The second and fifth aspects of this invention are pharmaceutical compositions comprising a compound of the first or fourth aspect of this invention and optionally a pharmaceutically acceptable excipient.

The compounds of the first and fourth aspects of this invention may be administered by any route suitable to the subject being treated and the nature of the subject's condition. Routes of administration include administration by injection, including intravenous, intraperitoneal, intramuscular, and subcutaneous injection, by transmucosal or transdermal delivery, through topical applications, nasal spray, suppository and the like or may be administered orally. Formulations may optionally be liposomal formulations, emulsions, formulations designed to administer the drug across mucosal membranes or transdermal formulations. Suitable formulations for each of these methods of administration may be found, for example, in *Remington: The Science and Practice of Pharmacy*, 20th ed., A. Gennaro, ed., Lippincott Williams & Wilkins, Philadelphia, Pa., U.S.A. Typical formulations will be either oral or solutions for intravenous infusion. Typical dosage forms will be tablets or capsules for oral administration, solutions for intravenous infusion, and lyophilized powders for reconstitution as solutions for intravenous infusion.

Depending on the intended mode of administration, the pharmaceutical compositions may be in the form of solid, semi-solid or liquid dosage forms, preferably in unit dosage form suitable for single administration of a precise dosage. In addition to an effective amount of the active ingredient(s), the compositions may contain suitable pharmaceutically-acceptable excipients, including adjuvants which facilitate processing of the active compounds into preparations which can be used pharmaceutically. "Pharmaceutically acceptable excipient" refers to an excipient or mixture of excipients which does not interfere with the effectiveness of the biological activity of the active ingredient(s) and which is not toxic to the host to which it is administered.

For solid compositions, conventional excipients include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary excipients such as wetting or emulsifying agents, pH buffering agents and the like, for example, sodium acetate, sorbitan monolaurate, triethanolamine sodium acetate, triethanolamine oleate, etc.

For oral administration, the composition will generally take the form of a tablet or capsule, or it may be an aqueous or nonaqueous solution, suspension or syrup. Tablets and capsules are preferred oral administration forms. Tablets and capsules for oral use will generally include one or more commonly used excipients such as lactose and corn starch. Lubricating agents, such as magnesium stearate, are also typically added. When liquid suspensions are used, the active agent may be combined with emulsifying and suspending excipients. If desired, flavoring, coloring and/or sweetening agents may be added as well. Other optional excipients for incorporation into an oral formulation include preservatives, suspending agents, thickening agents, and the like.

Injectable formulations can be prepared in conventional forms, either as liquid solutions or suspensions, solid forms suitable for solubilization or suspension in liquid prior to injection, or as emulsions or liposomal formulations. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils, fatty esters or polyols are conventionally employed as solvents or suspending media.

The pharmaceutical compositions of this invention may also be formulated as lyophilized powders for parenteral administration. Powders may be reconstituted by addition of water or other aqueous medium and then further diluted with a suitable diluent prior to use. The liquid formulation is generally a buffered, isotonic, aqueous solution. Examples of suitable diluents are isotonic saline solution, 5% dextrose in water, and buffered sodium or ammonium acetate solution. Pharmaceutically acceptable solid or liquid excipients may be added to enhance or stabilize the composition, or to facilitate preparation of the composition.

Typically, a pharmaceutical composition of the present invention is packaged in a container with a label, or instructions, or both, indicating use of the pharmaceutical composition in the treatment of cancer.

The pharmaceutical composition may additionally contain one or more other pharmacologically active agents in addition to a compound of this invention. These additional active agents will typically be useful in treating cancer, or for enhancing the treatment of cancer by compounds of this invention.

Methods of Using the Compounds

The compounds of the first and fourth aspect of this invention have activity against human cancer cell lines, as demonstrated in the in vitro and in vivo Examples below, and are therefore considered to be useful as human cancer chemotherapeutic agents, for the treatment of human cancers.

Thus, the third and sixth aspects of this invention include methods of treating cancer in humans by administering a therapeutically effective amount of a compound of the first or fourth aspect of this invention, or a pharmaceutical composition of the second or fifth aspect of this invention, to the human. Optionally, the methods further comprise treating the human with another anticancer therapy, such as a therapy already conventional for the cancer being treated.

Cancers that are particularly treatable by the method of this invention are cancers with sensitivity to inducers of apoptosis, and more specifically those cancers that express or, particularly, overexpress one or more glutathione S-transferase isoenzymes. Cancers that express or overexpress one or more glutathione S-transferase isoenzymes when treated with other anticancer compounds or combination cancer chemotherapy regimens are especially treatable by the method of this invention. Such cancers include cancers of the brain, breast, bladder, cervix, colon and rectum, esophagus, head and neck, kidney, lung, liver, ovary, pancreas, prostate, and stomach; leukemias such as ALL, AML, AMML, CLL, CML, CMML, and hairy cell leukemia; Hodgkin's and non-Hodgkin's lymphomas; mesotheliomas, multiple myeloma; and sarcomas of bone and soft tissue. Cancers particularly treatable by the method of this invention include breast, ovarian, colorectal, and non-small cell lung cancers.

The amount of the compound of the first or fourth aspect of this invention that is administered to the human (either alone or, more usually, in a composition of the second or fifth aspect of this invention) should be a therapeutically effective amount when used alone or when used in conjunction with the another anticancer therapy (if the compound of the first or fourth aspect of this invention is administered in conjunction with another anticancer therapy); and similarly the amount of the another anticancer therapy that is administered to the mammal (if the compound of the first or fourth aspect of this invention is administered in conjunction with another anticancer therapy) should be a therapeutically effective amount when used in conjunction with the compound of the first or fourth aspect of this invention. However, the therapeutically effective amount of either the compound of the first or fourth aspect of this invention and the amount of the another anticancer therapy when administered in combination cancer chemotherapy may each be less than the amount which would be therapeutically effective if delivered to the human alone. It is common in cancer therapy, though, to use the maximum tolerated dose of the or each therapy, with a reduction only because of common toxicity of the therapies used or potentiation of the toxicity of one therapy by another. Because of the lack of cross-resistance of canfosfamide, for example, with several common chemotherapeutic agents, and its relative lack of clinically severe toxicity, especially its lack of clinically severe hematological toxicity, it is expected that compounds of the first and fourth aspect of this invention will be administrable at essentially their maximum tolerated dose as a single agent, and no reduction in the amount of the another anticancer therapy will be required.

The compounds of the first and fourth aspects of this invention, or pharmaceutical compositions of the second and fifth aspects of this invention, are thus used to treat cancer in humans requiring such treatment, by administering a therapeutically effective amount of the chosen compound or composition. Therapeutically effective amounts of compounds of the invention are in the range of 10-10,000 mg/m$^2$, for example, 30-3000 mg/m$^2$ or 100-1000 mg/m$^2$. Dosing may be at 1-35 day intervals; for example, about 500-1000 mg/m$^2$ at 1-5 week intervals, especially at 1, 2, 3, or 4 week intervals, or at higher frequencies including as frequently as once/day for several (e.g. 5 or 7) days, with the dosing repeated every 2, 3, or 4 weeks, or constant infusion for a period of 6-72 hours, also with the dosing repeated every 2, 3, or 4 weeks. Suitable dosages and dose frequencies will be readily determinable by a person of ordinary skill in the art having regard to that skill and this disclosure. No unacceptable toxicological effects are expected when compounds of the invention are administered in accordance with the present invention.

Suitable dosing for the other anticancer therapy (if the compound of the first or fourth aspect of this invention is used in combination) will be the dosing already established for that therapy, as described in such documents as those listed in paragraph [0042]. Such dosing varies widely with the therapy: for example, capecitabine (2500 mg/m$^2$ orally) is dosed twice daily for 2 weeks on and 1 week off, imatinib mesylate (400 or 600 mg/day orally) is dosed daily, rituximab is dosed weekly, paclitaxel (135-175 mg/m$^2$) and docetaxel (60-100 mg/m$^2$) are dosed weekly to every three weeks, carboplatin (4-6 mg/mL·min) is dosed once every 3 or 4 weeks (though the doses may be split and administered over several days), nitrosourea alkylating agents such as carmustine are dosed as infrequently as once every 6 weeks. Radiotherapy may be administered as frequently as weekly (or even within that split into smaller dosages administered daily).

A person of ordinary skill in the art of cancer therapy will be able to ascertain a therapeutically effective amount of the compound of the first or second aspect of this invention and a therapeutically effective amount of another anticancer therapy for a given cancer and stage of disease without undue experimentation and in reliance upon personal knowledge and the disclosure of this application.

Combination therapies include the combination administration of a compound of the first aspect of this invention with a platinum compound such as carboplatin or cisplatin, optionally in further combination with gemcitabine or a taxane such as docetaxel or paclitaxel; with gemcitabine; with a taxane; with an anthracycline such as doxorubicin or liposomal doxorubicin; with oxaliplatin, optionally in further combination with capecitabine or fluorouracil/leucovorin; and with gemcitabine or a platinum compound such as carboplatin or cisplatin, in further combination with a vinca alkaloid such as vinorelbine.

EXAMPLES

The following examples illustrate the preparation of compounds of this invention, and their activity in predictive in vitro and in vivo anticancer assays.

SYNTHETIC EXAMPLES

The compounds of this invention are prepared by conventional methods of organic chemistry. See, for example, Larock, "Comprehensive Organic Transformations", Wiley-VCH, New York, N.Y., U.S.A. In some cases, protective groups may be introduced and later removed. Suitable protective groups for amino, hydroxyl, and carboxyl groups are described in Greene et al. "Protective Groups in Organic Synthesis", 2nd ed., 1991, John Wiley and Sons, New York, N.Y., U.S.A. The compounds of this invention can be synthesized, generally following the synthetic schemes illustrated earlier in this application, as shown in the following examples or by modifying the exemplified syntheses by means known to those of ordinary skill in the art.

The synthetic examples below show compounds where R in formulae A, B, C, BB, and CC are all 2-chloroethyl. It will be apparent that compounds where R is other than 2-chloroethyl may be produced by parallel methods: for example:

(a) compounds where R is 2-bromoethyl may be made by reacting bis(2-bromoethyl)amine, POCl$_3$, and ethylene glycol to produce 2-hydroxyethyl tetrakis(2-bromoethyl) phosphorodiamidate, esterifying to an appropriate sulfonate ester, and using that to alkylate the thiols of formula A$^1$ and B$^1$ or 2,2'-thiodiethanol to form the compounds of formulae AA, BB, and CC;

(b) compounds where R is 2-(Z-sulfonyloxy)ethyl may be made by using bis(2-hydroxyethylamine) instead of bis(2-bromoethylamine) in the process of (a) above, then forming the sulfonate esters; and (c) compounds where the R groups are not identical (e.g. where one R on each amine is 2-chloroethyl and the other is hydrogen) may be made by using the appropriate amine (e.g. 2-chloroethylamine) in the process of (a) above.

A person of ordinary skill in the art will have no difficulty, having regard to that skill and this disclosure, in preparing compounds where R is other than 2-chloroethyl.

It will also be apparent that when the $R^1$ group of formula A or the $R^2$ group of formula B contain reactive (e.g. amino, carboxy) groups, that these groups may be elaborated to produce other compounds. This elaboration of the $R^1$ and $R^2$ groups may take place at the thiol stage (elaboration of the $R^1$ group of formula $A^1$ or of the $R^2$ group of formula $B^1$), or at the thioethyl phosphorodiamidate stage (elaboration of the $R^1$ group of formula AA or of the $R^2$ group of formula BB), or at the sulfonylethyl phosphorodiamidate stage (elaboration of the $R^1$ group of formula A or of the $R^2$ group of formula B). All such elaborations may be performed by synthetic methods known per se. A person of ordinary skill in the art will have no difficulty, having regard to that skill and this disclosure, in elaborating $R^1$ and $R^2$ groups from those readily available to prepare the full range of the compounds of this invention.

For example, considering elaborated analogs of compound 13A (the preparation of which is illustrated in Synthetic Example 1 below): 2-mercaptoacetic acid may be alkylated with a phosphorodiamidate such as 2-(4-bromobenzenesulfonyloxy)ethyl tetrakis(2-chloroethyl)-phosphorodiamidate to give compounds such as 2-[[2-[[bis[bis(2-chloroethyl)amino]phosphinyl]oxy]-ethyl]thio]acetic acid. This may be oxidized to 2-[[2-[[bis[bis(2-chloroethyl)amino]phosphinyl]oxy]-ethyl]sulfonyl]acetic acid, compound 14A. The acid may, either before or after oxidation, be reacted with an amine in the presence of a base and coupling reagent, to form an amide. Compound 13A could be made this way, though it may be directly prepared as described below, and compounds 18A to 24A are examples of compounds that may be made this way. Similar compounds having longer carbon chains between the carboxy group and the sulfonyl group, e.g. compound 29A and derivatives such as compounds 53A to 59A, may be prepared by starting with 3-mercaptopropionic acid and similar thio-acids. Esters may similarly be prepared by esterification. Conversely, starting with a mercaptoalkylamine (temporarily protected at the amine), alkylating the sulfur atom, oxidizing, and deprotecting, allows the preparation of reverse amides. Also, starting with 2-mercaptoethanol and alkylating and oxidizing allows the preparation of compound 16A, and the hydroxy group can be esterified to give reverse esters. Similar elaborations can be made from compounds such as 139A (allowing the preparation of compounds such as compounds 154A to 178A) and 141A (allowing the preparation of compounds such as compounds 142A to 152A).

For example, considering elaborated analogs of compound 70A (the preparation of which is illustrated in Synthetic Example 2 below):

(a) 3-[[2-[[bis[bis(2-chloroethyl)amino]phosphinyl]oxy]ethyl]thio]-N-tert-butoxycarbonyl-L-alanine may be converted to the corresponding alaninamide by reaction with an amine (typically in excess) in an aprotic solvent (e.g. dichloromethane+dimethylformamide) in the presence of a coupling reagent (e.g. HBTU). That alaninamide may then be oxidized to a compound of formula A by any of the oxidation methods described, and then may be deprotected at the amine as described in Synthetic Example 2. Compounds 87A to 89A are examples of compounds that may be made this way. Alternatively, the alaninamide may be deprotected at the amine and reacted with, for example, an alkane- or arenesulfonyl chloride (typically in excess) in an aprotic solvent in the presence of an organic base to form the corresponding sulfonamide at the alanine nitrogen, then oxidized to form a compound of formula A. Alternatively, the alanine may first be oxidized, then deprotected, and then elaborated at the sulfone stage. Compounds 95A to 97A are examples of compounds that may be made this way; and/or (b) an ester of 3-[[2-[[bis[bis(2-chloroethyl)amino]phosphinyl]oxy]ethyl]thio]-N-tert-butoxycarbonyl-L-alanine (for example, prepared by starting the synthesis with the corresponding L-cysteine ester) may be converted to the sulfonamide at the alanine nitrogen, and then oxidized to form a compound of formula A. Compounds 79A to 81A are examples of compounds that may be made this way. The esters may be hydrolyzed to give the corresponding acids. Compounds 103A to 105A are examples of compounds that may be made this way. Alternatively, the alanine ester may be oxidized, then deprotected, and then elaborated at the sulfone stage.

Compounds of Formula A.

Synthetic Example 1

Preparation of N-methyl-2-[[2-[[bis[bis(2-chloroethyl)amino]phosphinyl]-oxy]ethyl]sulfonyl]acetamide, compound 13A N-methyl-2-[[2-[[bis[bis(2-chloroethyl)amino]phosphinyl]oxy]ethyl]thio]acetamide. To a solution of crushed sodium hydroxide pellets, 2.28 g (57 mmol), in 20 mL anhydrous methanol cooled in an ice bath was added N-methyl-2-mercaptoacetamide, 3 g (28.5 mmol), slowly, followed by the addition of 20 mL anhydrous toluene and 2-(4-bromobenzenesulfonyloxy)ethyl tetrakis(2-chloroethyl)-phosphorodiamidate, 34.4 mL of 0.83 M solution in toluene (28.5 mmol), while maintaining the temperature at 5° C. or less. After stirring for about 30 min, the reaction mixture became a white slurry. It was stirred at 5° C. to room temperature overnight. LC-MS analysis indicated all the starting material, N-methyl-2-mercaptoacetamide, was consumed and the desired product was formed as a major product. The mixture was filtered and the filtrate was concentrated. The residue was partitioned between diisopropyl acetate and brine. The aqueous phase was further extracted with diisopropyl acetate three times, and the combined organic phases were dried ($MgSO_4$) and evaporated to give the crude product, which was purified by column chromatography on a silica column using hexane/acetate and acetate/methanol as eluting solvents to afford N-methyl-2-[[2-[[bis[bis(2-chloroethyl)amino]phosphinyl]oxy]ethyl]thio]acetamide as a light yellow oil, 12 g (88% yield). $^1$H NMR (DMSO): δ 7.90 (bs, 1H) 4.05 (m, 2H), 3.71 (m, 8H), 3.33 (m, 8H), 3.12 (s, 2H), 2.87 (m, 2H), 2.59 (d, 3H, J=4.7 Hz), 2.76 (m, 1H). Mass spectrum (LC-MS): m/z 496 $[C_{13}H_{26}Cl_4N_3O_3PS+H]^+$.

N-methyl-2-[[2-[[bis[bis(2-chloroethyl)amino]phosphinyl]oxy]ethyl]sulfonyl]acetamide. N-methyl-2-[[2-[[bis[bis(2-chloroethyl)amino]phosphinyl]oxy]ethyl]thio]acetamide, 7.4 g (15.6 mmol), was dissolved in 5 mL dichloromethane in a 50-mL round-bottom flask, and the solution was cooled in ice bath. Peracetic acid, 7.4 g of 32 wt. % (31.2 mmol) was added slowly and the reaction mixture was stirred at 0° C. to room temperature overnight. LC-MS analysis indicated the reaction was complete with no starting material remaining. The solvent was evaporated and the oily residue was partitioned between isopropyl acetate and aqueous sodium bicarbonate. The organic phase was further washed with aqueous sodium bicarbonate and brine, dried (MgSO$_4$) and evaporated to give the product as an oil. Treatment with ethyl ether caused the precipitation of a white solid, which was collected by filtration, washed with a small amount of ethyl ether and dried under high vacuum to give the final product, N-methyl-2-[[2-[[bis[bis(2-chloroethyl)amino]phosphinyl]oxy]ethyl]sulfonyl]acetamide, compound 13A, 5.37 g (68%). The filtrate was saved for later purification. HPLC coupled with ELSD (Evaporative Light Scattering Detection) analysis of the product showed a purity of 99%. $^1$H NMR (CDCl$_3$): δ 6.59 (bs, 1H), 4.53 (m, 2H), 3.95 (s, 2H), 3.65 (m, 10H), 3.47 (m, 8H), 2.88 (d, 3H, J=4.7 Hz). $^{31}$P NMR (CDCl$_3$): δ 17.7 (s, 1P). Mass spectrum (LC-MS): m/z 508 [C$_{13}$H$_{26}$Cl$_4$N$_3$O$_5$PS+H]$^+$.

Synthetic Example 2

Preparation of 3-[[2-[[bis[bis(2-chloroethyl)amino]phosphinyl]oxy]ethyl]-sulfonyl]-L-alanine, compound 70A, as its hydrochloride salt 3-[[2-[[Bis[bis(2-chloroethyl)amino]phosphinyl]oxy]ethyl]thio]-N-tert-butoxycarbonyl-L-alanine. Crushed sodium hydroxide pellets, 1.2 g (29.8 mmol), and 30 mL methanol were added to a 100-mL round-bottom flask, and the mixture stirred until the sodium hydroxide had dissolved. The solution was then cooled to 5° C., and N-tert-butoxycarbonyl-L-cysteine, 3 g (13.6 mmol), and 2-(4-bromobenzenesulfonyloxy)ethyl tetrakis(2-chloroethyl)phosphorodiamidate, 8.25 mL of 1 M solution in toluene (8.25 mmol), were added while maintaining the temperature at 5° C. or less. The reaction mixture was stirred under nitrogen for 2 hours at room temperature, and after about 40 minutes, the solution became a white slurry. HPLC analysis of the reaction mixture showed 96.7% 3-[[2-[[bis[bis(2-chloroethyl)amino]phosphinyl]oxy]ethyl]thio]-N-tert-butoxycarbonyl-L-alanine, 3.3% di-N-tert-butoxycarbonyl-L-cystine, and no remaining 2-(4-bromobenzenesulfonyloxy)ethyl tetrakis(2-chloroethyl)phosphorodiamidate. The pH of the mixture was adjusted to 6-7 with 1 M phosphoric acid, and the mixture was concentrated under high vacuum to a white residue, 9.22 g. The residue was dissolved in 30 mL water and washed with 30 mL and 15 mL isopropyl acetate. The aqueous layer was diluted with 38 mL isopropyl acetate and the pH of the mixture adjusted to 5.15-5.20 with 1 M phosphoric acid. The layers were separated and the isopropyl acetate layer retained. The aqueous layer was extracted twice more with isopropyl acetate, and the isopropyl acetate extracts combined, washed with water (2×3.5 mL, 2×10.5 mL), and concentrated under high vacuum to give 3-[[2-[[bis[bis(2-chloroethyl)amino]phosphinyl]oxy]ethyl]thio]-N-tert-butoxycarbonyl-L-alanine as a clear viscous oil, 5.60 g (70% yield). HPLC analysis of the product showed a purity of 97.3%. $^1$H NMR: δ 7.05-7.18 (m, 1H), 4.04 (m, 3H), 3.70 (m, 8H), 3.33 (m, 8H), 2.92 (m, 1H), 2.81 (m, 1H), 2.76 (m, 1H). $^{13}$C NMR: δ 172.3, 172.0, 155.3, 78.2, 66.9, 63.7, 56.1, 53.7, 48.4, 48.4, 42.3, 32.8, 31.9, 31.8, 28.1, 25.4, 21.5. $^{31}$P NMR: δ 17.1 (s, 1P). Mass spectrum: m/z 592 [C$_{18}$H$_{34}$Cl$_4$N$_3$O$_6$PS−H]$^-$, 777, 439.

3-[[2-[[Bis[bis(2-chloroethyl)amino]phosphinyl]oxy]ethyl]sulfonyl]-N-tert-butoxycarbonyl-L-alanine. 3-[[2-[[bis[bis(2-chloroethyl)amino]phosphinyl]oxy]ethyl]thio]-N-tert-butoxycarbonyl-L-alanine, 2.5 g (4.21 mmol), was dissolved in 15 mL isopropyl acetate in a 50-mL round-bottom flask, and the solution was cooled to 5° C. Peracetic acid, 2.22 mL of 32 wt. % (2.5 g, 10.5 mmol), was added, and the reaction mixture was stirred for 7.5 hours at 0-5° C. After 5 hours, HPLC analysis of the reaction mixture showed no starting material. The reaction mixture was washed with water (2×6.5 mL), aqueous sodium hydrosulfite (6.5 mL of 1 M), and again with water (2×6.5 mL). The isopropyl acetate layer tested negative for peroxides with starch/iodine paper, and was concentrated under high vacuum overnight to give 3-[[2-[[bis[bis(2-chloroethyl)amino]phosphinyl]oxy]ethyl]sulfonyl]-N-tert-butoxycarbonyl-L-alanine as a white, sticky foam, 1.94 g (74% yield). HPLC analysis of the product showed a purity of 96.7%. $^1$H NMR: δ 7.29-7.38 (m, 1H), 4.43 (m, 1H), 4.29 (m, 2H), 3.71 (m, 8H), 3.57 (m, 4H), 3.34 (m, 8H), 1.39 (s, 9H). $^{13}$C NMR: δ 171.9, 171.2, 155.1, 78.6, 66.9, 58.0, 54.2, 53.6, 53.5, 48.3, 48.3, 42.3, 28.1, 21.6, 21.0, 21.0. $^{31}$P NMR: δ 17.4 (s, 1P). Mass spectrum: m/z 624 [C$_{18}$H$_{34}$Cl$_4$N$_3$O$_8$PS−H]$^-$.

3-[[2-[[Bis[bis(2-chloroethyl)amino]phosphinyl]oxy]ethyl]sulfonyl]-L-alanine. 3-[[2-[[Bis[bis(2-chloroethyl)amino]phosphinyl]oxy]ethyl]sulfonyl]-N-tert-butoxycarbonyl-L-alanine, 1.82 g (2.91 mmol), was dissolved in 18 mL ethyl acetate, and to this solution was added hydrogen chloride, 1.75 mL of 2 M solution in diethyl ether (3.5 mmol); and the resulting mixture stirred under nitrogen overnight at room temperature. HPLC analysis of the reaction mixture showed that the reaction was incomplete (20.8% product), so an additional 0.9 equivalents of hydrogen chloride solution was added and the reaction mixture stirred for an additional 4 days, resulting in the formation of a slurry. HPLC analysis of the reaction mixture showed 99.7% product and 0.3% starting material. The slurry was filtered under nitrogen, washed with ethyl acetate, and dried under nitrogen for 3 hours to give 3-[[2-[[bis[bis(2-chloroethyl)amino]phosphinyl]oxy]ethyl]sulfonyl]-L-alanine, compound 70A, as the hydrochloride salt, off-white solid, 0.90 g (55% yield). HPLC analysis of the product showed a purity of 99.7%. $^1$H NMR: δ 8.50-9.10 (bs, 3H), 4.43 (m, 1H), 4.32 (m, 2H), 3.93-3.97 (m, 1H), 3.70-3.80 (m, 11H), 3.34 (m, 8H). $^{13}$C NMR: δ 168.2, 58.0, 57.9, 53.8, 53.7, 53.0, 48.3, 48.3, 47.1, 42.3. $^{31}$P NMR: δ 17.5 (s, 1P). Mass spectrum: m/z 526 [C$_{13}$H$_{26}$Cl$_4$N$_3$O$_6$PS+H]$^+$.

Synthetic Example 3

Preparation of α-[[2-[[bis[bis(2-chloroethyl)amino]phosphinyl]oxy]ethyl]-sulfonyl]toluene, compound 128A α-[[2-[[Bis[bis(2-chloroethyl)amino]phosphinyl]oxy]ethyl]thio]toluene. Sodium hydroxide, 6.4 g (161 mmol), was dissolved in 100 mL methanol under nitrogen at room temperature, and α-toluenethiol, 9.52 mL (10 g, 80.5 mmol), was added. After the resulting mixture was stirred for 5 minutes, 2-(4-bromobenzenesulfonyloxy)ethyl tetrakis(2-chloroethyl)phosphorodiamidate, 80.5 mL of 1 M solution in toluene (80.5 mmol), was added with stirring. A precipitate formed within 1 minute of the addition, and stirring was continued. Analysis of the reaction after 2 hours showed that the reaction was nearly complete, and stirring was continued overnight at room temperature. Analysis then showed that the reaction was complete, and stirring was stopped and the reaction mixture allowed to stand and then filtered to remove the precipitated sodium 4-bromobenzenesulfonate. The methanol was removed from the filtrate by evaporation and the residue was dissolved in 250 mL isopropyl acetate. The isopropyl acetate solution was washed with aqueous sodium hydroxide (100 mL of 1 M), water (100 mL), and brine (100 mL), and was then dried over anhydrous sodium sulfate and filtered. The isopropyl acetate was removed by vacuum evaporation to give an oil, which was dried under vacuum at 40° C. overnight, giving 40.4 g of α-[[2-[[bis[bis(2-chloroethyl)amino]phosphinyl]oxy]ethyl]thio]toluene as an orange oil containing residual toluene. HPLC analysis of the product showed a purity of 96.8%. $^1$H NMR: δ 7.16-7.33 (m, 5H), 4.04-4.06 (m, 2H), 3.74 (s, 2H), 3.60-3.65 (m, 8H), 3.36-3.43 (m, 8H), 2.69 (t, 2H).

α-[[2-[[Bis[bis(2-chloroethyl)amino]phosphinyl]oxy]ethyl]sulfonyl]toluene. α-[[2-[[Bis[bis(2-chloroethyl)amino]phosphinyl]oxy]ethyl]thio]toluene, 9.2 g (18.7 mmol), was dissolved in 20 mL concentrated acetic acid in a 100-mL round-bottom flask, and the solution cooled to 5° C. Peracetic acid, 7.9 mL of 32 wt. % (8.9 g, 37.5 mmol), was added dropwise over 20 minutes. The reaction mixture was allowed to warm to room temperature and stirred for 16 hours, and was then concentrated under reduced pressure on a rotary evaporator to give a yellow oil. The oil was dissolved in 100 mL dichloromethane, and 300 mL hexanes was added, giving a milky white solution, which was allowed to stand for 18 hours. The solution was vacuum filtered and the white solid residue was washed with hexanes (3×50 mL), then dried under high vacuum for 18 hours to give α-[[2-[[bis[bis(2-chloroethyl)amino]phosphinyl]oxy]ethyl]sulfonyl]toluene, as a white solid, 8.2 g (15.5 mmol, 83% yield). HPLC analysis of the product showed a purity of 96.4%. $^1$H NMR: δ 7.40-7.42 (m, 5H), 4.54 (s, 2H), 4.24-4.29 (q, 2H), 3.67-3.73 (m, 8H), 3.51 (t, 2H), 3.29-3.34 (m, 8H). $^{13}$C NMR: δ 131.9, 129.2, 128.8, 59.6, 58.9, 49.0, 43.0, 40.8, 39.6. $^{31}$P NMR: δ 17.3 (s, 1P). Mass spectrum: m/z 529 [$C_{17}H_{27}Cl_4N_2O_4PS$+H]$^+$.

Synthetic Example 4

Preparation of N-{2-[[2-[[bis[bis(2-chloroethyl)amino]phosphinyl]oxy]-ethyl]sulfonyl]acetyl}-L-phenylalanine, compound 15A 2-[[2-[[bis[bis(2-chloroethyl)amino]phosphinyl]oxy]ethyl]thio]acetic acid. Methyl 2-mercapto-acetate, 2.6 mL (28.5 mmol), was dissolved in 10 mL dry methanol, and sodium hydroxide, 2.24 mL of 25 M solution (56 mmol), and 10 mL methanol were added, followed by 2-(4-bromobenzene-sulfonyloxy)ethyl tetrakis(2-chloroethyl)phosphorodiamidate, 26 mL of 1 M solution in toluene (26 mmol) with stirring, and a further 20 mL methanol. A white precipitate formed immediately, and a further 30 mL methanol was added to enable easy stirring overnight. The solid was filtered, and an additional 2 mL of the sodium hydroxide solution added to the filtrate and stirred for 2 hours. The basic solution was washed with ethyl acetate, then hydrochloric acid added until the solution became cloudy. This solution was extracted three times with ethyl acetate, and the combined ethyl acetate extracts backwashed with water, dilute hydrochloric acid, water, and brine, and then dried over $Na_2SO_4$ and concentrated, to give 7.31 g of 2-[[2-[[bis[bis(2-chloroethyl)amino]phosphinyl]oxy]ethyl]thio]acetic acid as an oil that solidified on standing. The identity was verified by $^1$H NMR.

N-{2-[[2-[[bis[bis(2-chloroethyl)amino]phosphinyl]oxy]ethyl]thio]acetyl}-L-phenylalanine. L-Phenylalanine tert-butyl ester hydrochloride, 1.2 mg (4.5 mmol), was partitioned between ethyl acetate and aqueous sodium bicarbonate, washed with water and brine, then dried. This was added to 2-[[2-[[bis[bis(2-chloroethyl)amino]phosphinyl]oxy]ethyl]thio]acetic acid, 1.76 g (3.8 mmol), followed by 1.4 mL diisopropylamine (8.0 mmol) and HBTU, 1.46 g (3.85 mmol). The mixture was stirred for several hours at room temperature. The mixture was filtered, washed with 1 M sodium hydroxide, potassium bisulfate, and brine; then treated with 25% trifluoroacetic acid in dichloromethane to hydrolyze the tert-butyl ester. The mixture was then concentrated to give N-{2-[[2-[[bis[bis(2-chloroethyl)amino]-phosphinyl]oxy]ethyl]thio]acetyl}-L-phenylalanine.

N-{2-[[2-[[bis[bis(2-chloroethyl)amino]phosphinyl]oxy]ethyl]sulfonyl]acetyl}-L-phenylalanine. The N-{2-[[2-[[bis[bis(2-chloroethyl)amino]phosphinyl]oxy]ethyl]thio]acetyl}-L-phenylalanine prepared above was dissolved in 20 mL ethyl acetate and oxidized using 3 mL 32% peracetic acid using the procedure of Synthetic Example 1. After washing the ethyl acetate solution with sodium hydrosulfite, water, and brine, it was dried, concentrated, chromatographed, and the fractions combined, stirred with ethanol, and lyophilized to give N-{2-[[2-[[bis[bis(2-chloroethyl)amino]phosphinyl]oxy]ethyl]sulfonyl]-acetyl}-L-phenylalanine, 1.5 g (62% yield), as a white solid. Purity was verified.

Synthetic Example 5

Preparation of α-[[2-[[bis[bis(2-chloroethyl)amino]phosphinyl]oxy]ethyl]-sulfonyl]-4-[(ethoxycarbonylmethyl)aminocarbonyl]toluene, compound 172A α-[[2-[[Bis[bis(2-chloroethyl)amino]phosphinyl]oxy]ethyl]thio]-4-carboxytoluene. 4-(Thiomethyl)benzoic acid was prepared from methyl 4-(bromomethyl)benzoate using the procedure of Org. Syn. Coll. Vol. 3, page 363 (reaction with thiourea in ethanol, followed by hydrolysis of the ester with aqueous sodium hydroxide). 4-(Thiomethyl)benzoic acid, 2 g, was alkylated with 2-(4-bromobenzenesulfonyloxy)ethyl tetrakis(2-chloroethyl)phosphorodiamidate, 15.8 mL of 0.83 M, in 10 mL methanol and 6.25 mL of 4 M sodium hydroxide in methanol. The resulting product after filtration and concentration was a pale yellow oil, which was dissolved in saturated aqueous sodium bicarbonate and washed twice with 100 mL isopropyl acetate. The aqueous extracts were combined, acidified to pH ~1 with sulfuric acid, and back extracted twice with into 100 mL isopropyl acetate. The isopropyl acetate layers were combined, dried over $MgSO_4$, filtered, and concentrated under vacuum to give α-[[2-[[bis[bis(2-chloroethyl)amino]phosphinyl]oxy]ethyl]thio]-4-carboxytoluene as a pale yellow oil, 5.4 g, with product identity verified by LC-MS.

α-[[2-[[bis[bis(2-chloroethyl)amino]phosphinyl]oxy]ethyl]thio]-4-[(ethoxycarbonylmethyl)-aminocarbonyl]toluene. To α-[[2-[[Bis[bis(2-chloroethyl)amino]phosphinyl]oxy]ethyl]thio]-4-carboxytoluene, 411 mg, in 10 mL dichloromethane was added 400 µL diisopropylethylamine and glycine ethyl ester, 212 mg. The solution was cooled to 0° C. and HBTU, 317 mg, in 2 mL dimethylformamide was added, after which the mixture was allowed to warm to room temperature. The reaction mixture was diluted with dichloromethane, then washed 3 times with 1 M hydrochloric acid, 5 times with saturated aqueous sodium bicarbonate, and once with brine. The organic layer was dried over $MgSO_4$, filtered, and the solvents removed under vacuum to give α-[[2-[[bis[bis(2-chloroethyl)amino]phosphinyl]oxy]ethyl]thio]-4-[(ethoxycarbonylmethyl)aminocarbonyl]toluene as a clear oil, 411 mg, with product identity verified by LC-MS.

α-[[2-[[bis[bis(2-chloroethyl)amino]phosphinyl]oxy]ethyl]sulfonyl]-4-[(ethoxycarbonylmethyl)-aminocarbonyl]toluene. The α-[[2-[[bis[bis(2-chloroethyl)amino]phosphinyl]oxy]ethyl]thio]-4-[(ethoxycarbonylmethyl)aminocarbonyl]toluene, 411 mg, was dissolved in 6 mL isopropyl acetate and oxidized with 414 µL 32% peracetic acid solution as described in previous Synthetic Examples. After workup, α-[[2-[[bis[bis(2-chloroethyl)amino]phosphinyl]oxy]ethyl]sulfonyl]-4-[(ethoxycarbonylmethyl)-aminocarbonyl]toluene was isolated as a clear oil, 449 mg. Product identity from a parallel run was verified by LC-MS.

Synthetic Example 6

Preparation of N-(methanesulfonyl)-3-[[2-[[bis[bis(2-chloroethyl)amino]-phosphinyl]oxy]ethyl]sulfonyl]-L-alanine methyl ester, compound 79A 3-[[2-[[Bis[bis(2-chloroethyl)amino]phosphinyl]oxy]ethyl]thio]-L-alanine methyl ester. 3-[[2-[[Bis[bis(2-chloroethyl)amino]phosphinyl]oxy]ethyl]thio]-N-tert-butoxycarbonyl-L-alanine, 5.0 g (8.4 mmol), prepared as in Synthetic Example 2, was dissolved in 35 mL dichloromethane, and 5.3 mL (42 mmol) chlorotrimethyl silane added with stirring at 0° C., followed by 80 mL methanol. With continued stirring, the mixture was allowed to warm to room temperature, then stirred overnight. The solvents were then removed under vacuum to give a light yellow oil. This was dissolved in ethyl acetate and precipitated with diethyl ether. Filtration and concentration of the filtrate gave two fractions of 3-[[2-[[bis[bis(2-chloroethyl)amino]phosphinyl]oxy]ethyl]thio]-L-alanine methyl ester, totaling 4.87 g. Purity (96%) and identity were verified by ELSD and LC-MS (m/z 508 (M+2+H)$^+$).

N-(Methanesulfonyl)-3-[[2-[[bis[bis(2-chloroethyl)amino]phosphinyl]oxy]ethyl]thio]-L-alanine methyl ester. 3-[[2-[[Bis[bis(2-chloroethyl)amino]phosphinyl]oxy]ethyl]thio]-L-alanine methyl ester, 400 mg (0.8 mmol), was dissolved in 4 mL anhydrous tetrahydrofuran, and 550 μL (3.2 mmol) diisopropylethylamine added, followed by methanesulfonyl chloride, 181 mg (1.6 mmol). The reaction mixture was purged with argon and stirred overnight. After adding a further 275 μL (1.6 mmol) diisopropylethylamine, then tris(2-aminoethyl)amine-polystyrene resin, 480 mg (1.6 mmol), the mixture was agitated for 6 hours, then filtered and the filtrate evaporated to dryness under vacuum, giving N-(methanesulfonyl)-3-[[2-[[bis[bis(2-chloroethyl)amino]phosphinyl]oxy]ethyl]thio]-L-alanine methyl ester, 397 mg. Purity was verified with ELSD and identity verified with $^1$H and $^{31}$P NMR.

N-(Methanesulfonyl)-3-[[2-[[bis[bis(2-chloroethyl)amino]phosphinyl]oxy]ethyl]sulfonyl]-L-alanine methyl ester. N-(Methanesulfonyl)-3-[[2-[[bis[bis(2-chloroethyl)amino]phosphinyl]oxy]ethyl]thio]-L-alanine methyl ester, 369 mg (0.63 mmol), was dissolved in 5 mL ethyl acetate and oxidized with 662 μL 32% peracetic acid solution as described in previous Synthetic Examples. After workup, N-(Methanesulfonyl)-3-[[2-[[bis[bis(2-chloroethyl)amino]phosphinyl]oxy]ethyl]sulfonyl]-L-alanine methyl ester, compound 79A, was isolated as a clear oil, 358 mg (87%). Purity was verified with ELSD and identity verified with LC-MS (m/z 618 (M+2+H)$^+$).

Other compounds of formula A as shown in the tables below were prepared by similar methods. Note that the largest peak in the mass spectrum for compounds of formula A is at 2 greater than the peak corresponding to the exact mass (the mass determined based on the most common isotopes of the atoms making up the molecule) because of the presence of 4 chlorine atoms in the molecule: the intensities of the three largest peaks are 3:4:2 at M, M+2, and M+4.

The following compounds of formula A were prepared:

| Compound | Structure | Exact mass | MS |
|---|---|---|---|
| 1A | 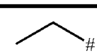 | 464 | |
| 2A | 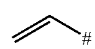 | 462 | 463 (M + H$^+$) |
| 3A | 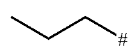 | 478 | 479 (M + H$^+$) |
| 4A | 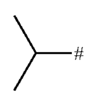 | 478 | |
| 5A | 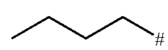 | 492 | 495 (M + 2 + H$^+$) |
| 6A | 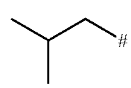 | 492 | |
| 7A | 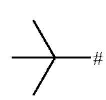 | 492 | 493 (M + H$^+$) |
| 8A | 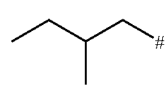 | 506 | |
| 9A | 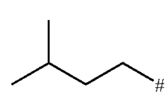 | 506 | |
| 10A | 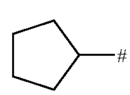 | 504 | |

-continued
| Compound | Structure | Exact mass | MS |
|---|---|---|---|
| 11A | 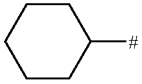 | 518 | |
| 12A | 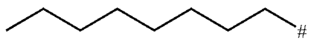 | 548 | 549 (M + H$^+$) |
| 13A | 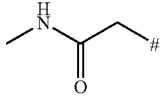 | 507 | 508 (M + H$^+$) |
| 14A | 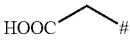 | 494 | |
| 15A | 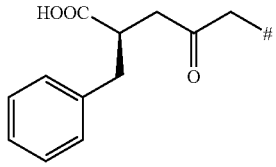 | 641 | 642 (M + H$^+$) |
| 16A | 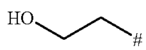 | 480 | 481 (M + H$^+$) |
| 17A | 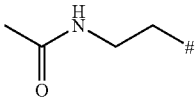 | 521 | 524 (M + 2 + H$^+$) |
| 18A | 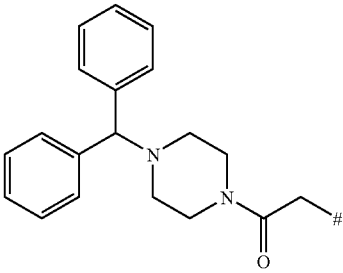 | 728 | 729 (M + H$^+$) |
| 19A | 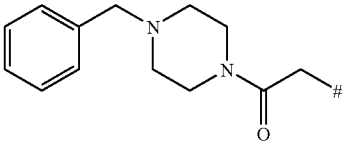 | 652 | 653 (M + H$^+$) |
| 20A | 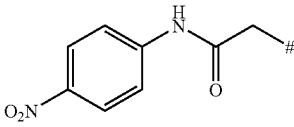 | 615 | 615 (M + H$^+$) |
| 21A | 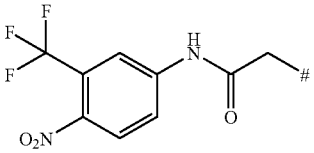 | 682 | 683 (M + H$^+$) |

-continued

| Compound | Structure | Exact mass | MS |
|---|---|---|---|
| 22A | (4-methylpiperazin-1-yl)-C(=O)-CH2-# | 576 | 577 (M + H+) |
| 23A | morpholine-CH2CH2-NH-C(=O)-CH2-# | 606 | 607 (M + H+) |
| 24A | pyridin-2-yl-NH-C(=O)-CH2-# | 570 | 571 (M + H+) |
| 25A | tBuO-C(=O)-CH(CH2Ph)-NH-C(=O)-CH2-# | 697 | 698 (M + H+) |
| 26A | HOOC-CH(CH2Ph)-NH-C(=O)-CH2-# | 641 | 644 (M + 2 + H+) |
| 27A | tBuO-C(=O)-CH(CH2CH2CH2CH2-NH(t-BOC))-NH-C(=O)-CH2-# | 780 | 680 (M-BOC) |
| 28A | tBuO-C(=O)-CH2-N(CH3)-C(=O)-CH2-# | 623 | 624 (M + H+) |
| 29A | HOOC-CH2CH2-# | 508 | 509 (M + H) |
| 30A | MeO-C(=O)-C6H4-NH-C(=O)-CH2-# | 627 | 628 (M + H+) |
| 31A | tBuO-C(=O)-CH(CH2CH2CH2CH2-NH2)-NH-C(=O)-CH2-# | 622 | |

| Compound | Structure | Exact mass | MS |
|---|---|---|---|
| 32A | (L)-ornithine-like: HOOC-CH(NH₂)-CH₂CH₂-CH₂-NH-C(=O)-CH₂-# | 608 | |
| 33A | 4-(HOOC)-C₆H₄-NH-C(=O)-CH₂-# | 613 | |
| 34A | HOOC-CH₂-N(CH₃)-C(=O)-CH₂-# | 565 | 568 (M + 2 + H⁺) |
| 35A | tBuO-C(=O)-CH(Ph)-NH-C(=O)-CH₂-# | 683 | 630 (M + 2 + Bu + H⁺) |
| 36A | HOOC-CH(Ph)-NH-C(=O)-CH₂-# | 627 | 630 (M + 2 + H⁺) |
| 37A | tBuO-C(=O)-CH₂CH₂-NH-C(=O)-CH₂-# | 621 | 622 (M + 2 − H⁻) |
| 38A | tBuO-C(=O)-CH₂-NH-C(=O)-CH₂-# | 607 | 608 (M + 2 − H⁻) |
| 39A | HOOC-CH₂CH₂-NH-C(=O)-CH₂-# | 565 | 568 (M + H) |
| 40A | HOOC-CH₂-NH-C(=O)-CH₂-# | 551 | 554 (M + H) |
| 41A | H₂N-C(=O)-CH(CH₂-C(=O)-OtBu)-NH-C(=O)-CH₂-# | 664 | 665 (M + 2 − H⁻) |

-continued

| Compound | Structure | Exact mass | MS |
|---|---|---|---|
| 42A | 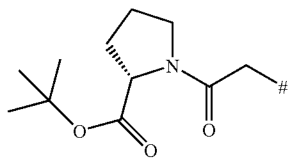 | 647 | 648 (M + 2 − H⁻) |
| 43A | 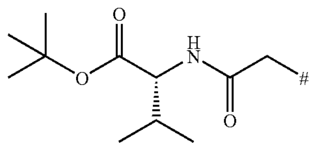 | 649 | 650 (M + 2 − H⁻) |
| 44A | 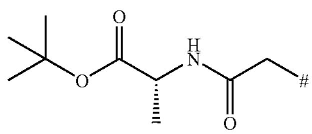 | 621 | 622 (M + 2 − H⁻) |
| 45A | 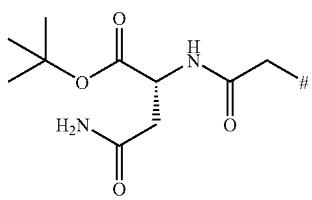 | 664 | 665 (M + 2 − H⁻) |
| 46A | 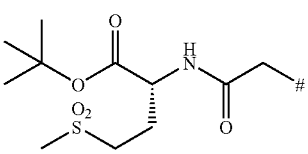 | 713 | 714 (M + 2 − H⁻) |
| 47A | 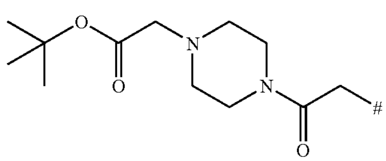 | 676 | 677 (M + 2 − H⁻) |
| 48A | 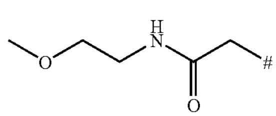 | 551 | 552 (M + H⁺) |
| 49A | 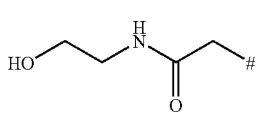 | 537 | 538 (M + H⁺) |
| 50A | 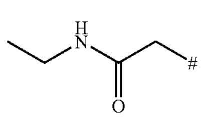 | 521 | 522 (M + H⁺) |
| 51A | 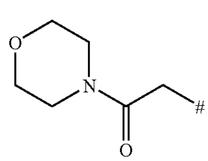 | 563 | 564 (M + H⁺) |

-continued

| Compound | Structure | Exact mass | MS |
|---|---|---|---|
| 52A | (4-hydroxypiperidin-1-yl)-C(O)-CH2-# | 577 | 578 (M + H+) |
| 53A | CH3-NH-C(O)-CH2CH2-# | 521 | 522 (M + H+) |
| 54A | CH3CH2-NH-C(O)-CH2CH2-# | 535 | 536 (M + H+) |
| 55A | cyclopropyl-NH-C(O)-CH2CH2-# | 547 | 548 (M + H+) |
| 56A | HO-CH2CH2-NH-C(O)-CH2CH2-# | 551 | 552 (M + H+) |
| 57A | CH3O-CH2CH2-NH-C(O)-CH2CH2-# | 565 | 566 (M + H+) |
| 58A | morpholino-C(O)-CH2CH2-# | 577 | 578 (M + H+) |
| 59A | (4-hydroxypiperidin-1-yl)-C(O)-CH2CH2-# | 591 | 592 (M + H+) |
| 60A | cyclopropyl-NH-C(O)-CH2-# | 533 | 534 (M + H+) |
| 61A | H2N-C(O)-CH(CH2COOH)-NH-C(O)-CH2-# | 608 | 611 (M + 2 + H+) |
| 62A | (2-carboxypyrrolidin-1-yl)-C(O)-CH2-# | 591 | 594 (M + 2 + H+) |

-continued

| Compound | Structure | Exact mass | MS |
|---|---|---|---|
| 63A | HOOC-CH(iPr)-NH-C(=O)-CH2-# | 593 | 596 (M + 2 + H+) |
| 64A | HOOC-CH(Me)-NH-C(=O)-CH2-# | 565 | 568 (M + 2 + H+) |
| 65A | HOOC-CH(CH2C(=O)NH2)-NH-C(=O)-CH2-# | 608 | 611 (M + 2 + H+) |
| 66A | HOOC-CH(CH2CH2S(O2)Me)-NH-C(=O)-CH2-# | 657 | 660 (M + 2 + H+) |
| 67A | methyl 4-(acylamino)thiophene-3-carboxylate, acyl = -C(=O)-CH2-# | 633 | 636 (M + 2 + H+) |
| 68A | HN-piperazine-N-C(=O)-CH2-# | 562 | 565 (M + 2 + H+) |
| 69A | HOCH2CH2-N-piperazine-N-C(=O)-CH2-# | 606 | 607 (M + H+) |
| 70A | H2N-CH(CH2#)-COOH | 523 | 526 (M + 2 + H+) |
| 71A | (t-BOC)NH-CH(CH2#)-COOH | 623 | |
| 72A | H2N-CH(CH2#)-C(=O)-O-Et | 551 | |

-continued

| Compound | Structure | Exact mass | MS |
|---|---|---|---|
| 73A | ![Ac-NH-CH(COOH)-CH2-#] | 565 | 568 (M + 2 + H⁺) |
| 74A | ![Ac-NH-CH(COOH)-CH(tBu)-#] | 593 | 594 (M + H⁺) |
| 75A | ![H2N-CH(COOH)-CH(tBu)-#] | 551 | 552 (M + H⁺) |
| 76A | ![H2N-CH(COOH)-CH(tBu)-#] | 551 | 552 (M + H⁺) |
| 77A | ![H2N-CH(COOH)-CH2CH2-#] | 537 | |
| 78A | ![H2N-CH(CONH2)-CH2-#] | 522 | 523 (M + H⁺) |
| 79A | ![MeSO2-NH-CH(COOMe)-CH2-#] | 615 | 618 (M + 2 + H⁺) |
| 80A | ![PhSO2-NH-CH(COOMe)-CH2-#] | 677 | 680 (M + 2 + H⁺) |
| 81A | ![4-Cl-C6H4-SO2-NH-CH(COOMe)-CH2-#] | 711 | 714 (M + 2 + H⁺) |
| 82A | ![H2N-CH(COOBn)-CH2-#] | 612 | 615 (M + 2 + H⁺) |

-continued

| Compound | Structure | Exact mass | MS |
|---|---|---|---|
| 83A | (t-BOC)-NH-CH(#)-C(O)-N(morpholine) | 692 | 595 (M + 2-BOC + H$^+$) |
| 84A | (t-BOC)-NH-CH(#)-C(O)-NH-iPr | 664 | 665 (M + H$^+$) |
| 85A | (t-BOC)-NH-CH(#)-C(O)-N(piperazine)-C(O)-furan | 785 | 787 (M + 2$^+$) |
| 86A | (t-BOC)-NH-CH(#)-C(O)-NH-CH$_2$CH$_2$OH | 666 | 668 (M + 2$^+$) |
| 87A | H$_2$N-CH(#)-C(O)-N(morpholine) | 592 | 594 (M + 2$^+$) |
| 88A | H$_2$N-CH(#)-C(O)-NH-CH$_2$CH$_2$OH | 566 | 568 (M + 2$^+$) |
| 89A | H$_2$N-CH(#)-C(O)-NH-iPr | 564 | 566 (M + 2$^+$) |
| 90A | H$_2$N-CH(#)-C(O)-N(piperazine)-C(O)-furan | 685 | 687 (M + 2$^+$) |
| 91A | PhSO$_2$-NH-CH(#)-C(O)-NH-CH$_2$-Ph | 752 | 753 (M + H$^+$) |

-continued

| Compound | Structure | Exact mass | MS |
|---|---|---|---|
| 92A | 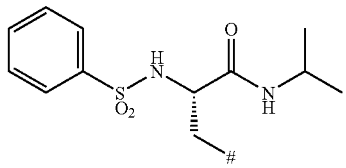 | 704 | 706 (M + 2+) |
| 93A | 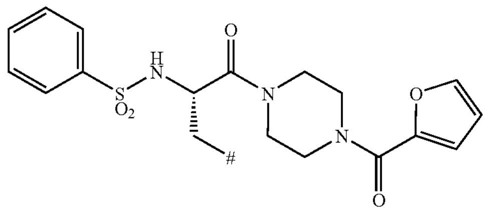 | 825 | 826 (M + H+) |
| 94A | 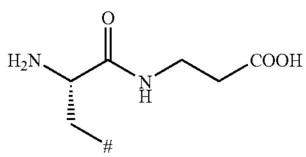 | 594 | 597 (M + 2 + H+) |
| 95A | 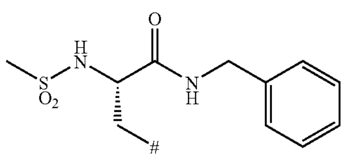 | 690 | 691 (M + H+) |
| 96A | 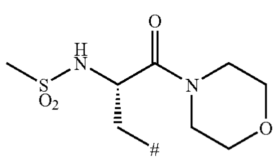 | 670 | 671 (M + H+) |
| 97A | 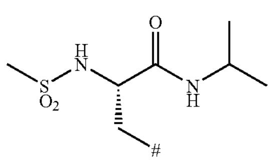 | 642 | 643 (M + H+) |
| 98A | 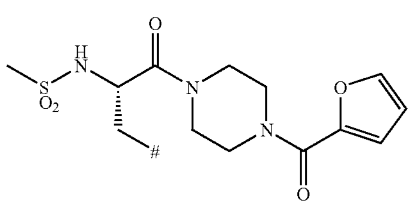 | 763 | 765 (M + 2+) |
| 99A | 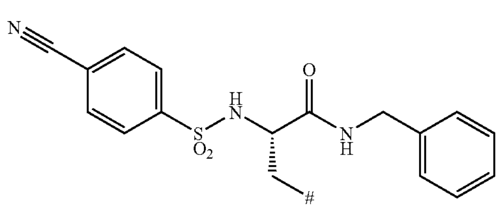 | 777 | 778 (M + H+) |

-continued

| Compound | Structure | Exact mass | MS |
|---|---|---|---|
| 100A | 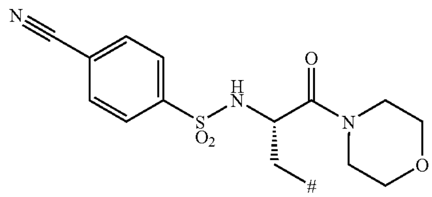 | 757 | 759 (M + 2$^+$) |
| 101A | 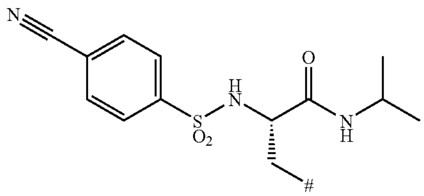 | 729 | 730 (M + H$^+$) |
| 102A | 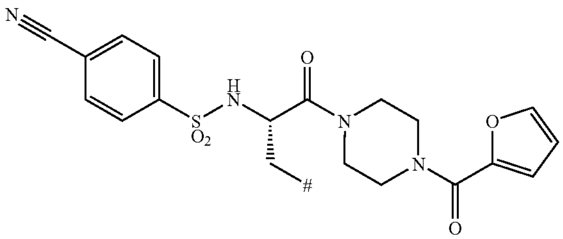 | 850 | 852 (M + 2$^+$) |
| 103A | 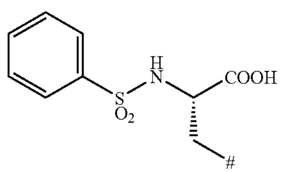 | 663 | 664 (M + H$^+$) |
| 104A | 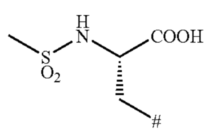 | 601 | 602 (M + 2 − H$^-$) |
| 105A | 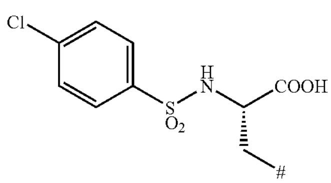 | 697 | 698 (M + 2 − H$^-$) |
| 106A | 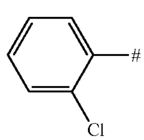 | 546 | 549 (M + 2 + H$^+$) |
| 107A | 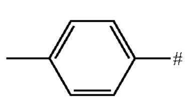 | 526 | 527 (M + H$^+$) |
| 108A | 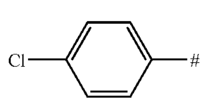 | 546 | 549 (M + 2 + H$^+$) |
| 109A | 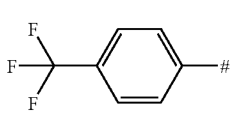 | 580 | 581 (M + H$^+$) |

-continued

| Compound | Structure | Exact mass | MS |
|---|---|---|---|
| 110A | 3-methylphenyl-# | 526 | 527 (M + H$^+$) |
| 111A | 4-fluorophenyl-# | 530 | 531 (M + H$^+$) |
| 112A | 3,4-dichlorophenyl-# | 580 | 583 (M + 2 + H$^+$) |
| 113A | biphenyl-4-yl-# | 588 | 589 (M + H$^+$) |
| 114A | 4-tert-butylphenyl-# | 568 | 571 (M + 2 + H$^+$) |
| 115A | 4-methoxyphenyl-# (H$_3$CO) | 542 | 545 (M + 2 + H$^+$) |
| 116A | 3-(trifluoromethyl)phenyl-# | 580 | 583 (M + 2 + H$^+$) |
| 117A | phenyl-# | 512 | 515 (M + 2 + H$^+$) |
| 118A | 2-carboxyphenyl-# (COOH) | 556 | 557 (M + H$^+$) |
| 119A | 3-carboxyphenyl-# (HOOC) | 556 | 555 (M − H$^-$) |
| 120A | pyridin-4-yl-# | 513 | 514 (M + H$^+$) |
| 121A | benzothiazol-2-yl-# | 569 | 570 (M + H$^+$) |
| 122A | 1-methylimidazol-2-yl-# | 516 | 517 (M + H$^+$) |

-continued

| Compound | Structure | Exact mass | MS |
|---|---|---|---|
| 123A | 5-methylpyrimidin-2-yl-# | 528 | 529 (M + H$^+$) |
| 124A | pyridin-2-yl-# | 513 | 514 (M + H$^+$) |
| 125A | 9H-purin-6-yl-# | 554 | 555 (M + H$^+$) |
| 126A | 2-carboxypyridin-3-yl-# | 557 | 560 (M + 2 + H$^+$) |
| 127A | 9H-purin-2-yl-# | 554 | 555 (M + H$^+$) |
| 128A | benzyl-# | 526 | 528 (M + 2$^+$) |
| 129A | 3-methylbenzyl-# | 540 | 543 (M + 2 + H$^+$) |
| 130A | 4-methylbenzyl-# | 540 | 543 (M + 2 + H$^+$) |
| 131A | 4-chlorobenzyl-# | 560 | 563 (M + 2 + H$^+$) |
| 132A | 4-fluorobenzyl-# | 544 | 547 (M + 2 + H$^+$) |
| 133A | 3-(trifluoromethyl)benzyl-# | 584 | 597 (M + 2 + H$^+$) |
| 134A | 3,4-dichlorobenzyl-# | 595 | 598 (M + 2 + H$^+$) |
| 135A | 2,4-dichlorobenzyl-# | 595 | 598 (M + 2 + H$^+$) |

| Compound | Structure | Exact mass | MS |
|---|---|---|---|
| 136A | 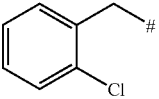 | 560 | 563 (M + 2 + H$^+$) |
| 137A | 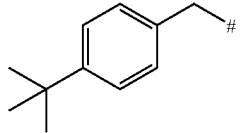 | 582 | 585 (M + 2 + H$^+$) |
| 138A | 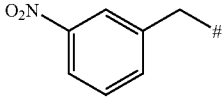 | 571 | 574 (M + 2 + H$^+$) |
| 139A | 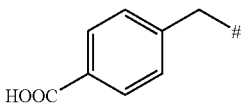 | 570 | 569 (M − H$^-$) |
| 140A | 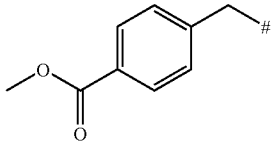 | 584 | 585 (M + H$^+$) |
| 141A | 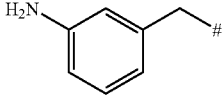 | 541 | 544 (M + 2 + H$^+$) |
| 142A | 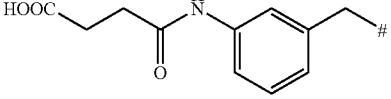 | 641 | 644 (M + 2 + H$^+$) |
| 143A | 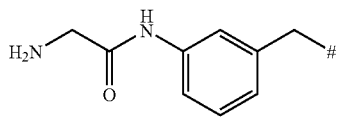 | 598 | 601 (M + 2 + H$^+$) |
| 144A | 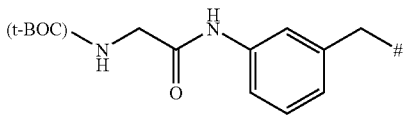 | 698 | 601 (M + 2-BOC + H$^+$) |
| 145A | 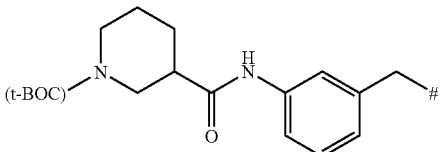 | 826 | |
| 146A | 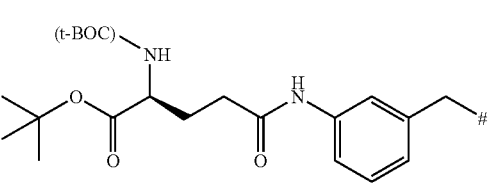 | 752 | 655 (M + 2-BOC + H$^+$) |

-continued

| Compound | Structure | Exact mass | MS |
|---|---|---|---|
| 147A | (structure: HOOC-CH(NH2)-CH2-CH2-C(O)-NH-C6H4(3-)-CH2-#) | 670 | 673 (M + 2 + H⁺) |
| 148A | (structure: piperidine-3-C(O)-NH-C6H4(3-)-CH2-#) | 652 | 655 (M + 2 + H⁺) |
| 149A | (structure: 4-methylpiperazine-1-C(O)-NH-C6H4(3-)-CH2-#) | 652 | 653 (M + H⁺) |
| 150A | (structure: 4-methyl-4-oxide-piperazine-1-C(O)-NH-C6H4(3-)-CH2-#) | 668 | 669 (M + H⁺) |
| 151A | (structure: 4-(2-hydroxyethyl)piperazine-1-C(O)-NH-C6H4(3-)-CH2-#) | 682 | 683 (M + H⁺) |
| 152A | (structure: 4-(2-hydroxyethyl)-4-oxide-piperazine-1-C(O)-NH-C6H4(3-)-CH2-#) | 698 | 699 (M + H⁺) |
| 153A | (structure: 4-cyanobenzyl-#) | 551 | 552 (M + H⁺) |
| 154A | (structure: morpholine-4-C(O)-C6H4(4-)-CH2-#) | 639 | |
| 155A | (structure: N,N-dimethyl-4-carbamoylbenzyl-#) | 597 | 598 (M + H⁺) |

-continued
| Compound | Structure | Exact mass | MS |
|---|---|---|---|
| 156A | 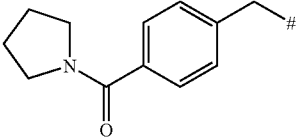 | 623 | 624 (M + H+) |
| 157A | 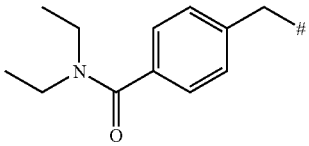 | 625 | 626 (M + H+) |
| 158A | 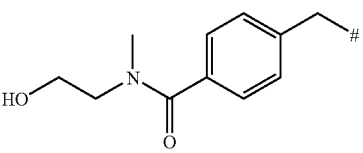 | 627 | 628 (M + H+) |
| 159A | 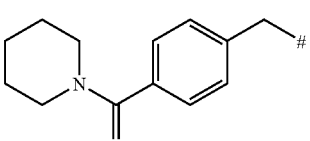 | 637 | 638 (M + H+) |
| 160A | 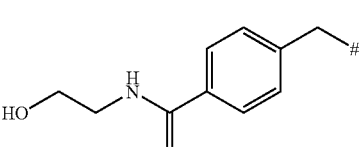 | 613 | 614 (M + H+) |
| 161A | 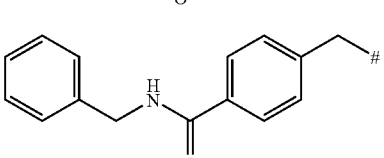 | 659 | 660 (M + H+) |
| 162A | 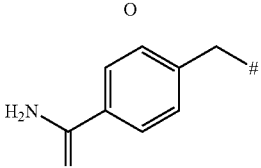 | 569 | 570 (M + H+) |
| 163A | 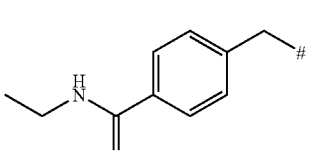 | 597 | 598 (M + H+) |
| 164A | 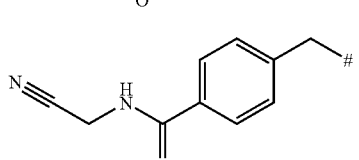 | 608 | 609 (M + H+) |
| 165A | 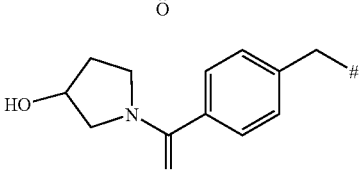 | 639 | 640 (M + H+) |

-continued
| Compound | Structure | Exact mass | MS |
|---|---|---|---|
| 166A | 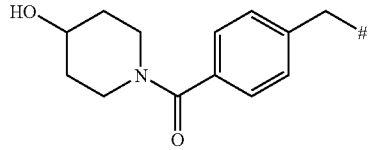 | 653 | 654 (M + H+) |
| 167A | 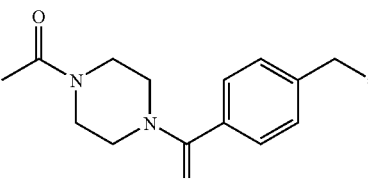 | 680 | 681 (M + H+) |
| 168A | 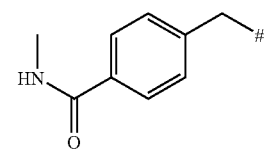 | 583 | 584 (M + H+) |
| 169A | 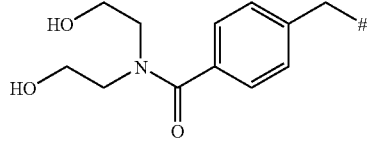 | 657 | 658 (M + H+) |
| 170A | 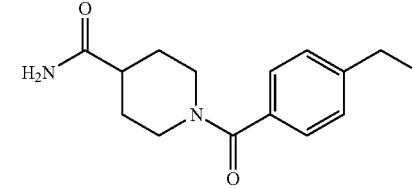 | 680 | 681 (M + H+) |
| 171A | 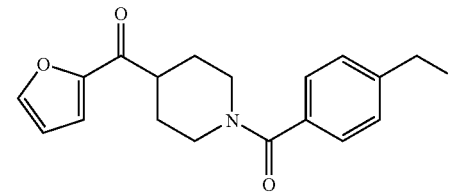 | 732 | 733 (M + H+) |
| 172A | 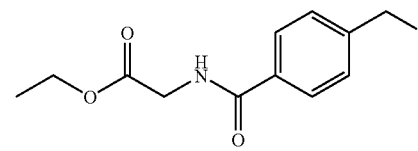 | 655 | 656 (M + H+) |
| 173A | 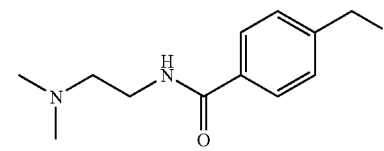 | 640 | (M + H+) |
| 174A | 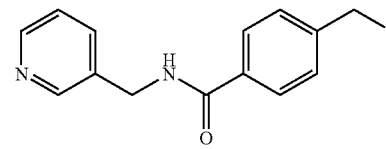 | 660 | 661 (M + H+) |

-continued

| Compound | Structure | Exact mass | MS |
|---|---|---|---|
| 175A | morpholine-N-CH₂CH₂CH₂-NH-C(O)-C₆H₄-CH₂-# | 696 | 697 (M + H⁺) |
| 176A | 2-pyridyl-piperazine-C(O)-C₆H₄-CH₂-# | 715 | 716 (M + H⁺) |
| 177A | benzyl-piperazine-C(O)-C₆H₄-CH₂-# | 728 | 729 (M + H⁺) |
| 178A | acetyl-piperazine-C(O)-C₆H₄-CH₂-# | 655 | 656 (M + H⁺) |
| 179A | furan-2-yl-CH₂-# | 516 | 517 (M + H⁺) |
| 180A | thiophen-2-yl-CH₂-# | 532 | 533 (M + H⁺) |
| 181A | pyridin-2-yl-CH₂-# | 527 | 528 (M + H⁺) |
| 182A | pyridin-2-yl N-oxide-CH₂-# | 543 | 544 (M + H⁺) |
| 183A | 2-methyl-3-hydroxy-4-hydroxymethyl-pyridin-5-yl-CH₂-# | 587 | 588 (M + H⁺) |

-continued

| Compound | Structure | Exact mass | MS |
|---|---|---|---|
| 184A | 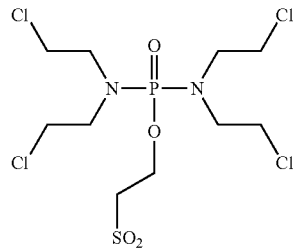 | 603 | 604 (M + H⁺) | represents the bis[bis(2-chloroethyl)amino]phosphinyl]oxy]ethyl]sulfonyl group of the formula attached to the rest of the molecule at the sulfur atom.
t-BOC represents the tert-butoxycarbonyl group.

All of these compounds of formula A were analyzed to confirm identity and purity, using HPLC for purity, and one or more of mass spectrometry and NMR ($^{1}$H, $^{13}$C, and/or $^{31}$P) for identity, and were confirmed to be the expected product in good purity. Other compounds of formula A may be similarly prepared.

Compounds of Formula BB and Formula B.

Synthetic Example 7

Preparation of 1,5-di[[2-[[bis[bis(2-chloroethyl)amino]phosphinyl]oxy]-ethyl]sulfonyl]naphthalene (compound 23B)

1,5-Di[[2-[[bis[bis(2-chloroethyl)amino]phosphinyl]oxy]ethyl]thio]naphthalene. 1,5-Naphthalenedithiol, 194 mg (1.009 mmol), was dissolved in 10 mL methanol and sodium hydroxide, 2 mL of 2 M solution in methanol (4 mmol); and 2-(4-bromobenzenesulfonyloxy)ethyl tetrakis(2-chloroethyl)phosphorodiamidate, 1.86 mL of 1 M solution in toluene (1.86 mmol) was added. The reaction mixture was stirred at room temperature, and after about 30 minutes a white precipitate had formed. The mixture was stirred overnight, then the precipitate filtered and the filtrate concentrated to a solid residue, which was extracted into ethyl acetate and washed with 1 N aqueous sodium hydroxide, water, and brine, then dried over anhydrous magnesium sulfate. The ethyl acetate was removed under vacuum, and the crude 1,5-di[[2-[[bis[bis(2-chloroethyl)amino]phosphinyl]oxy]ethyl]-thio]naphthalene was purified by flash chromatography (silica column, eluting with a gradient between 75% ethyl acetate/hexane and 100% ethyl acetate). The final 1,5-di[[2-[[bis[bis(2-chloroethyl)amino]-phosphinyl]oxy]ethyl]thio]naphthalene (compound 23BB) was a light yellow oil, yield 405 mg (42%), with product identity and purity verified by HPLC and NMR. Mass spectrum: m/z 937 [$C_{30}H_{46}Cl_8N_4O_4P_2S_2$+H⁺].

1,5-Di[[2-[[bis[bis(2-chloroethyl)amino]phosphinyl]oxy]ethyl]sulfonyl]naphthalene. 1,5-di [[2-[[bis[bis(2-chloroethyl)amino]phosphinyl]oxy]ethyl]thio]naphthalene, 324 mg (0.346 mmol) was dissolved in 10 mL ethyl acetate and cooled to 0-5° C. in an ice bath. To this was added 365 μL peracetic acid (32% by weight, 1.735 mmol), and the mixture kept at 0-5° C. for 1 hour, then allowed to warm to room temperature and allowed to stand overnight. The reaction mixture was dissolved in ethyl acetate, and the ethyl acetate layer separated, washed twice with water, twice with aqueous 1 M sodium dithionite, and twice more with water. The ethyl acetate was removed under vacuum, and the residue suspended in diethyl ether and sonicated for 30 minutes, then the ether poured off, with this procedure repeated once more. The 1,5-di[[2-[[bis[bis(2-chloroethyl)amino]phosphinyl]oxy]ethyl]sulfonyl]-naphthalene, compound 23B, was isolated as a white solid, 260 mg, with product identity and purity verified by HPLC and NMR. Mass spectrum: m/z 1001 [$C_{30}H_{46}Cl_8N_4O_8P_2S_2$+4+H⁺].

Other compounds of formula BB and formula B as shown in the tables below were prepared by similar methods. Note that the largest peak in the mass spectrum for compounds of formula B and formula BB (and also for compounds of formula C and formula CC) is at 4 greater than the peak corresponding to the exact mass because of the presence of 8 chlorine atoms in the molecule: the intensities of the 4 largest peaks are 4:9:10:6 at M, M+2, M+4, and M+6.

The following compounds of formula BB were prepared:

| Compound | Formula |
|---|---|
| 1BB | $-S-CH_2CH_2-S-$ |
| 2BB | (branched C4 dithio structure) |
| 3BB | $-S-CH_2CH_2CH_2-S-$ |
| 4BB | $-S-(CH_2)_4-S-$ |

| Compound | Formula |
|---|---|
| 5BB | $-headed structure: $-CH_2-CH(OH)-CH(OH)-CH_2-$ |
| 6BB | $-(CH_2)_5-$ |
| 7BB | $-(CH_2)_8-$ |
| 8BB | $-CH_2CH_2-O-CH_2CH_2-$ |
| 9BB | $-CH_2CH_2-O-CH_2CH_2-O-CH_2CH_2-$ |
| 10BB | 1,2-disubstituted benzene |
| 11BB | 1,3-disubstituted benzene |
| 12BB | 1,4-disubstituted benzene |
| 13BB | 1,2-bis(methylene)benzene |
| 14BB | 1,3-bis(methylene)benzene |
| 15BB | 1,4-bis(methylene)benzene |
| 16BB | 5-nitro-1,3-bis(methylene)benzene |
| 17BB | 5-amino-1,3-bis(methylene)benzene |
| 18BB | HOOC-CH₂CH₂-C(=O)-NH-(3,5-bis(methylene)phenyl) |
| 19BB | H₂N-CH₂-C(=O)-NH-(3,5-bis(methylene)phenyl) |
| 20BB | (CH₃)₂N-CH₂-C(=O)-NH-(3,5-bis(methylene)phenyl) |
| 21BB | piperidin-3-yl-C(=O)-NH-(3,5-bis(methylene)phenyl) |
| 22BB | pyridin-3-yl-C(=O)-NH-(3,5-bis(methylene)phenyl) |
| 23BB | 1,5-disubstituted naphthalene |

$represents the bis[bis(2-chloroethyl)amino]phosphinyl]oxy]ethyl]thio group of the formula $$\text{(ClCH}_2\text{CH}_2\text{)}_2\text{N-P(=O)(N(CH}_2\text{CH}_2\text{Cl)}_2\text{)-O-CH}_2\text{CH}_2\text{-S-}$$

attached to the rest of the molecule at the sulfur atom

All of these compounds of formula BB were analyzed to confirm identity and purity, using HPLC for purity, and one or more of mass spectrometry and NMR ($^1$H, $^{13}$C, and/or $^{31}$P) for identity, and were confirmed to be the expected product in good purity.

The following compounds of formula B were prepared:

| Compound | Formula | Exact Mass | MS |
|---|---|---|---|
| 1B | #∼∼# | 898 | |
| 2B | # with isopropyl branches # | 926 | 929 |
| 3B | #∼∼∼# | 912 | |
| 4B | #∼∼∼∼# | 926 | |
| 6B | #∼∼∼∼∼# | 940 | 942 |
| 7B | #∼∼∼∼∼∼∼# | 982 | 985 |
| 8B | #∼O∼# | 942 | 947 (M + 4 + H⁺) |
| 9B | #∼O∼O∼# | 986 | 991 (M + 4 + H⁺) |
| 10B | ortho-phenylene (#,#) | 946 | 951 (M + 4 + H⁺) |
| 11B | meta-phenylene (#,#) | 946 | 951 (M + 4 + H⁺) |
| 12B | para-phenylene (#,#) | 946 | 951 (M + 4 + H⁺) |
| 13B | ortho-xylylene (#CH₂-C₆H₄-CH₂#) | 974 | 979 (M + 4 + H⁺) |
| 14B | meta-xylylene | 974 | 979 (M + 4 + H⁺) |
| 15B | para-xylylene | 974 | 979 (M + 4 + H⁺) |
| 16B | O₂N-substituted meta-xylylene | 1019 | 1024 (M + 4 + H⁺) |

-continued

| Compound | Formula | Exact Mass | MS |
|---|---|---|---|
| 17B | H₂N-benzene-di(CH₂-#) | 989 | 994 (M + 4 + H⁺) |
| 18B | HOOC-CH₂CH₂-C(O)NH-benzene-di(CH₂-#) | 1089 | 1092 |
| 19B | H₂N-CH₂-C(O)NH-benzene-di(CH₂-#) | 1046 | 1051 (M + 4 + H⁺) |
| 20B | (CH₃)₂N-CH₂-C(O)NH-benzene-di(CH₂-#) | 1074 | 1079 (M + 4 + H⁺) |
| 21B | piperidine-3-C(O)NH-benzene-di(CH₂-#) | 1100 | 1105(M + 4 + H⁺) |
| 22B | pyridine-3-C(O)NH-benzene-di(CH₂-#) | 1094 | 1099 (M + 4 + H⁺) |
| 23B | naphthalene-1,5-di(#) | 996 | 1001 (M + 4 + H⁺) | represents the bis[bis(2-chloroethyl)amino]phosphinyl]oxy]ethyl]sulfonyl group of the formula

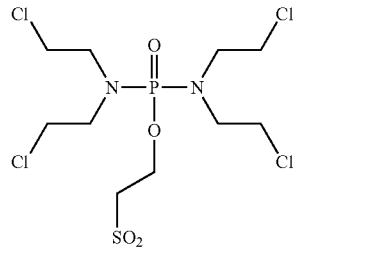

attached to the rest of the molecule at the sulfur atom

All of these compounds of formula B were analyzed to confirm identity and purity, using HPLC for purity, and one or more of mass spectrometry and NMR ($^1$H, $^{13}$C, and/or $^{31}$P) for identity, and were confirmed to be the expected product in good purity.

Other compounds of formula BB and formula B may be similarly prepared.

Compounds of Formula CC and Formula C.

Synthetic Example 8

Preparation of di[2-[[bis[bis(2-chloroethyl)amino]phosphinyl]oxy]ethyl]-sulfone, compound 1C N,N,N',N'-Tetrakis(2-chloroethyl)phosphorodiamidoyl chloride. Bis(2-chloroethyl)amine hydrochloride, 7.68 g (86 mmol), and phosphoryl trichloride, 4 mL (43 mmol), were suspended in 150 mL toluene, after which triethylamine, 12.6 mL (90 mmol), was added over 5 minutes. The reaction mixture was stirred at room temperature for 18 hours under nitrogen, then additional aliquots of bis(2-chloroethyl)amine hydrochloride, 7.68 g, and triethylamine, 12.6 mL, were added. The resulting mixture was heated to reflux and held at that temperature for 8 hours. After cooling, the precipitate was filtered and the filtrate concentrated under vacuum to remove volatiles. Crude N,N,N',N'-tetrakis(2-chloroethyl)phosphorodiamidoyl chloride was obtained was obtained as a dark brown oil, 15.45 g. The crude material was purified by flash column chromatography using 5-10% ethyl acetate/dichloromethane as eluent, and the pure fractions collected and volatiles removed, giving a total of 8.33 g N,N,N',N'-tetrakis(2-chloroethyl)phosphorodiamidoyl chloride as a light yellow oil, with identity verified by $^1$H and $^{31}$P NMR.

5-Hydroxy-3-thiapentyl N,N,N',N'-tetrakis(2-chloroethyl)phosphorodiamidate. N,N,N',N'-Tetrakis(2-chloroethyl)phosphorodiamidoyl chloride, 636 mg (1.745 mmol), and bis(2-hydroxyethyl)sulfide, 1 mL (9.67 mmol), were dissolved in 8 mL anhydrous tetrahydrofuran and cooled to 0-5° C. in an ice-water bath. Potassium tert-butoxide, 1.8 mL of 1 M solution in tetrahydrofuran (1.8 mmol), was added over a 10 minute period, and the reaction mixture kept at 0-5° C. for another 30 minutes. The reaction mixture was allowed to warm to room temperature and stirred at room temperature for 18 hours. It was then diluted with ethyl acetate; and the ethyl acetate layer separated, washed with 1 M hydrochloric acid and brine, then dried over anhydrous magnesium sulfate, and the ethyl acetate removed under vacuum. The crude 5-hydroxy-3-thiapentyl N,N,N',N'-tetrakis(2-chloroethyl)phosphorodiamidate was purified by column chromatography (silica gel, eluting with 25% ethyl acetate/hexane and 100% ethyl acetate), and obtained as a colorless oil, 335 mg (42.6% yield), identified by HPLC and $^1$H and $^{31}$P NMR.

Di[2-[[bis[bis(2-chloroethyl)amino]phosphinyl]oxy]ethyl]sulfide. 5-Hydroxy-3-thiapentyl N,N,N',N'-tetrakis(2-chloroethyl)phosphorodiamidate, 174 mg (0.387 mmol), and N,N,N',N'-tetrakis(2-chloroethyl)phosphorodiamidoyl chloride, 363 mg (0.996 mmol), were dissolved in 15 mL anhydrous tetrahydrofuran and cooled to 0-5° C. in an ice-water bath. Potassium tert-butoxide, 0.4 mL of 1 M solution in tetrahydrofuran (0.4 mmol), was added over a 10-15 minute period, and the reaction mixture kept at 0-5° C. for another 30 minutes under nitrogen. The reaction mixture was allowed to warm to room temperature and stirred at room temperature for 43 hours. Additional potassium tert-butoxide and N,N,N',N'-tetrakis(2-chloroethyl)phosphorodiamidoyl chloride were added over the next 4 days to drive the reaction to completion. After 4.5 days, the reaction mixture was diluted with ethyl acetate; and the ethyl acetate layer separated, washed with water and brine, then dried over anhydrous magnesium sulfate, and the ethyl acetate removed under vacuum. The crude di[2-[[bis[bis(2-chloroethyl)amino]phosphinyl]oxy]ethyl]sulfide, 630 mg, was twice purified by preparative HPLC, and the product fractions combined and lyophilized, giving di[2-[[bis[bis(2-chloroethyl)amino]phosphinyl]oxy]ethyl]sulfide, compound 1CC, as a colorless oil, compound 1CC, 56 mg (18% yield), identified by HPLC and $^1$H and $^{31}$P NMR. Mass spectrum: 779 ($C_{20}H_{40}Cl_8N_4O_4P_2S+4+H^+$).

Di[2-[[bis[bis(2-chloroethyl)amino]phosphinyl]oxy]ethyl]sulfone. The di[2-[[bis[bis(2-chloroethyl)amino]phosphinyl]oxy]ethyl]sulfide, 56 mg, from the previous reaction was dissolved in 10 mL ethyl acetate and cooled to 0-5° C. in an ice-water bath. Peracetic acid, 45 µL (0.214 mmol), was added, and the reaction mixture held at 0-5° C. for 1 hour then allowed to warm to room temperature and held for 2 hours to complete the reaction. The reaction mixture was diluted with ethyl acetate, and the ethyl acetate layer separated and washed twice with water, once with 1 M aqueous sodium dithionite, and twice more with water. The ethyl acetate was removed under vacuum to give di[2-[[bis[bis(2-chloroethyl)amino]phosphinyl]oxy]ethyl]sulfone, compound 1C, as a colorless oil, 54 mg (92.6% yield), identified by HPLC and $^1$H and $^{31}$P NMR. Mass spectrum: 811 ($C_{20}H_{40}Cl_8N_4O_6P_2S+4+H^+$).

IN VITRO EXAMPLES

The following examples illustrate the beneficial effect of the sulfonylethyl phosphorodiamidate esters of this invention against human cancer cell lines in vitro. These results are considered predictive of efficacy in human cancer chemotherapy, as other anticancer agents tested in these assays have shown anticancer activity in humans.

The human cancer cell lines DLD-1 (colorectal adenocarcinoma), LNCap (prostate carcinoma), and OVCAR-3 (ovarian carcinoma) were obtained from the American Type Culture Collection, Manassas, Va., U.S.A., and HL-60 (promyeloid myelocytic leukemia), MX-1 (breast carcinoma), P388, and P388ADR from the National Cancer Institute, Bethesda, Md., U.S.A. Carboplatin, doxorubicin, and melphalan were obtained from Sigma-Aldrich Chemical Company, St. Louis, Mo., U.S.A. The CellTiter-Glo assay kit was obtained from Promega Corporation, Madison, Wis., U.S.A., and the Cellular DNA Cytometric Analysis Reagent Kit from Roche Diagnostics Corporation, Indianapolis, Ind., U.S.A. Lambda DNA was obtained from New England Biolabs, Beverly, Mass., U.S.A., and SYBR-Gold from Molecular Probes, Inc., Eugene, Oreg., U.S.A. The DNeasy Tissue Kit was obtained from Qiagen Inc., Valencia, Calif., U.S.A., and AmpliTaq Gold DNA polymerase and PCR reagents from Applied Biosystems, Foster City, Calif., U.S.A. All products were used in accordance with manufacturer's directions. All assays were conducted in triplicate wells, with dimethyl sulfoxide (DMSO) solvent control. The extent of cell growth was expressed as a percentage of the signal from the solvent control wells.

In Vitro Example 1

Cytotoxicity/Growth Inhibition Assay

Log-phase cells were trypsinized, collected by centrifugation, and resuspended in a small volume of fresh medium, and the density of viable cells was determined following Trypan Blue staining. Cells were diluted in fresh media ($3\times10^3$ cells/mL for MX-1, $3\times10^3$ cells/mL for DLD-1, and $6\times10^3$ cells/mL for LNCap cells), the test compounds (concentrations between 0.1 and 200 µM, dissolved in DMSO, 50 µL) added immediately after dilution to achieve a final DMSO concentration of 0.5%, then the suspensions added at 150 µL/well to 96-well plates, and incubated for several hours to allow attachment in the case of adherent cells. The cells were cultured for approximately three doubling times (3 days for MX-1 and 4 days for DLD-1 and LNCap). The cells were then collected by centrifugation, and 100 µL of the culture supernatant was replaced by the CellTiter-Glo reagent. After incubation for 15 minutes at room temperature, and the plate was read with a luminometer. A number of compounds of formula BB and compound 1CC were tested in this assay and found to be active. Many compounds were found to be as potent as or more potent than canfosfamide.

Compounds of formula A showed the following activity in this assay:

| Compound | $IC_{50}$ (MX-1), µM | $IC_{50}$ (DLD-1), µM | $IC_{50}$ (LNCap), µM |
|---|---|---|---|
| 1A | 16.9 | 9.1 | 57.1 |
| 2A | 3.2 | 1.4 | 105.3 |
| 3A | 11.4 | 9.2 | 67.6 |
| 4A | 24.0 | 12.7 | 67.8 |
| 5A | 14.3 | 6.6 | 42.8 |
| 6A | 4.6 | 6.8 | 17.7 |
| 7A | 20.6 | 21.8 | 164.7 |
| 8A | 17.5 | 7.0 | 40.9 |
| 9A | 5.8 | 5.9 | 17.3 |
| 10A | 14.4 | 7.7 | 43.0 |
| 11A | 10.4 | 4.0 | 18.1 |
| 12A | 13.9 | 3.5 | 14.1 |
| 13A | 11.7 | 7.1 | 53.5 |
| 14A | 62.2 | 17.6 | 200.0 |
| 15A | 23.6 | 13.7 | 200.0 |
| 16A | 13.0 | 9.6 | 36.4 |
| 17A | 6.3 | 4.2 | 13.9 |
| 18A | 7.6 | 10.6 | 23.8 |
| 19A | 14.8 | 8.1 | 17.8 |
| 20A | 4.3 | 2.8 | 3.6 |
| 21A | 4.2 | 2.8 | 6.3 |
| 22A | 23.7 | 8.4 | 38.5 |
| 23A | 25.9 | 6.6 | 47.5 |
| 24A | 11.2 | 5.5 | 12.1 |
| 25A | 5.6 | 3.7 | 18.9 |
| 26A | 29.4 | 8.4 | 76.8 |
| 27A | 6.2 | 3.6 | 15.5 |
| 28A | 9.0 | 5.1 | 35.2 |
| 29A | 23.0 | 11.5 | 66.4 |
| 30A | 9.1 | 6.5 | 13.2 |
| 31A | 83.7 | 11.3 | |
| 32A | 41.2 | 11.3 | 177.0 |
| 33A | 20.6 | 8.6 | 98.6 |
| 34A | 9.0 | 12.0 | 97.2 |
| 35A | 6.6 | 5.0 | 24.8 |
| 36A | 12.3 | 5.4 | 200.0 |
| 37A | 8.0 | 8.0 | 28.9 |
| 38A | 8.0 | 7.6 | 23.3 |
| 39A | 30.8 | 13.3 | |
| 40A | 32.0 | 13.0 | |
| 41A | 29.3 | 10.8 | |
| 42A | 7.6 | 4.7 | |
| 43A | 7.2 | 3.9 | |
| 44A | 34.8 | 11.1 | |
| 45A | 7.3 | 8.4 | |
| 46A | 21.4 | 8.8 | |
| 47A | 15.9 | 9.3 | |
| 48A | 4.4 | 15.5 | |
| 49A | 29.0 | 11.6 | |
| 50A | 17.1 | 11.9 | |
| 51A | 6.9 | 6.7 | |
| 52A | 15.6 | 10.2 | |
| 53A | 11.3 | 8.4 | |
| 54A | 9.3 | 7.4 | |
| 55A | 14.7 | 10.1 | |
| 56A | 19.3 | 8.2 | |
| 57A | 18.0 | 10.1 | |
| 58A | 17.0 | 12.9 | |
| 59A | 25.4 | 15.1 | |
| 60A | 11.3 | 7.4 | |
| 61A | 30.9 | 20.0 | |
| 62A | 15.0 | 16.5 | |
| 63A | 10.0 | 17.2 | |
| 64A | 37.3 | 22.0 | |
| 65A | 31.8 | 21.4 | |
| 66A | 29.1 | 18.8 | |
| 67A | 2.8 | 1.9 | |
| 68A | 36.7 | 18.0 | |
| 69A | 34.6 | 14.1 | |
| 70A | 36.7 | 10.7 | |
| 73A | 29.6 | 18.0 | 73.2 |
| 74A | 46.7 | 27.2 | 200.0 |
| 75A | 33.1 | 7.6 | 184.7 |
| 76A | 23.2 | 6.6 | 99.7 |
| 77A | 21.3 | 8.0 | 139.7 |
| 78A | 18.8 | 6.3 | 200.0 |
| 79A | 88.0 | 26.6 | |
| 80A | 27.1 | 10.7 | 80.2 |
| 81A | 33.3 | 6.9 | 86.6 |
| 82A | 27.9 | 7.7 | 59.8 |
| 83A | 12.9 | 6.7 | 27.8 |
| 84A | 10.6 | 6.0 | 29.6 |
| 85A | 11.8 | 8.8 | 41.1 |
| 86A | 25.1 | 10.3 | 73.5 |
| 87A | 19.5 | 9.7 | 136.3 |
| 88A | 17.9 | 9.5 | 125.8 |
| 89A | 22.2 | 8.5 | 140.5 |
| 90A | 23.8 | 10.4 | 200.0 |
| 91A | 10.7 | 4.8 | 33.3 |
| 92A | 14.7 | 7.3 | 36.1 |
| 93A | 19.3 | 13.2 | 59.1 |
| 94A | 22.8 | 37.5 | 200.0 |
| 95A | 21.3 | 9.9 | 46.6 |
| 96A | 30.2 | 9.6 | 81.0 |
| 97A | 26.8 | 8.5 | 57.8 |
| 98A | 27.9 | 9.9 | 144.5 |
| 99A | 16.2 | 6.4 | 33.5 |
| 100A | 16.2 | 7.4 | 61.4 |
| 101A | 14.8 | 7.2 | 57.0 |
| 102A | 19.9 | 9.2 | 81.6 |
| 103A | 18.2 | 14.5 | 150.8 |
| 104A | 25.3 | 20.0 | 200.0 |
| 105A | 31.6 | 23.1 | 200.0 |
| 106A | 4.2 | 3.7 | 18.3 |
| 107A | 2.5 | 1.6 | 18.1 |
| 108A | 3.3 | 2.3 | 6.4 |
| 109A | 1.1 | 0.6 | 7.7 |
| 110A | 2.7 | 1.3 | 20.5 |
| 111A | 1.3 | 0.6 | 20.1 |
| 112A | 1.0 | 0.8 | 6.3 |
| 113A | 10.9 | 2.2 | 18.4 |
| 114A | 4.7 | 1.9 | 8.2 |
| 115A | 5.3 | 4.1 | 18.5 |
| 116A | 3.1 | 2.2 | 6.6 |
| 117A | 4.1 | 4.0 | 16.3 |
| 118A | 37.2 | 10.9 | 200.0 |
| 119A | 32.5 | 9.8 | 189.0 |
| 120A | 7.1 | 3.6 | 12.2 |
| 121A | 2.6 | 1.2 | 8.5 |
| 122A | 4.3 | 3.1 | 23.0 |
| 123A | 9.0 | 5.9 | 25.1 |
| 124A | 7.2 | 6.0 | 15.5 |
| 125A | 22.5 | 7.8 | 45.1 |
| 126A | 20.3 | 6.7 | 125.8 |
| 127A | 15.2 | 5.8 | 200.0 |
| 128A | 4.5 | 3.2 | |
| 129A | 7.1 | 5.4 | 16.3 |
| 130A | 6.5 | 5.1 | 22.0 |
| 131A | 5.2 | 3.6 | 6.9 |

-continued

| Compound | IC$_{50}$ (MX-1), μM | IC$_{50}$ (DLD-1), μM | IC$_{50}$ (LNCap), μM |
|---|---|---|---|
| 132A | 6.1 | 5.0 | 16.3 |
| 133A | 2.7 | 2.6 | 8.2 |
| 134A | 1.5 | 1.2 | 4.8 |
| 135A | 3.5 | 0.6 | 19.1 |
| 136A | 2.8 | 1.7 | 21.4 |
| 137A | 1.7 | 0.8 | 22.3 |
| 138A | 16.8 | 1.8 | 12.0 |
| 139A | 25.3 | 9.3 | 82.1 |
| 140A | 11.9 | 5.9 | 23.3 |
| 141A | 17.3 | 12.9 | 45.9 |
| 142A | 22.5 | 18.1 | 113.5 |
| 143A | 15.9 | 10.9 | 110.2 |
| 144A | 5.7 | 4.0 | 17.9 |
| 145A | 7.4 | 6.9 | 15.5 |
| 146A | 5.1 | 5.6 | 14.2 |
| 147A | 12.2 | 11.1 | 63.9 |
| 148A | 200.0 | 200.0 | |
| 149A | 94.3 | 7.5 | 200.0 |
| 150A | 31.3 | 7.6 | 118.2 |
| 151A | 28.6 | 6.1 | 158.1 |
| 152A | 37.6 | 9.3 | 108.0 |
| 153A | 3.0 | 1.8 | 6.9 |
| 154A | 5.5 | 5.8 | 26.2 |
| 155A | 2.6 | 10.7 | 42.4 |
| 156A | 4.8 | 3.5 | 31.4 |
| 157A | 3.1 | 2.3 | 29.6 |
| 158A | 35.4 | 17.5 | 85.2 |
| 159A | 5.3 | 3.5 | 24.4 |
| 160A | 33.2 | 13.9 | 103.9 |
| 161A | 7.4 | 3.7 | 11.7 |
| 162A | 7.1 | 4.7 | 55.1 |
| 163A | 4.8 | 4.8 | 28.5 |
| 164A | 10.7 | 5.8 | 45.9 |
| 165A | 21.9 | 8.0 | 113.9 |
| 166A | 20.5 | 6.3 | 90.2 |
| 167A | 23.7 | 7.7 | 61.0 |
| 168A | 7.9 | 5.7 | 24.2 |
| 169A | 34.5 | 7.6 | 144.4 |
| 170A | 31.4 | 10.8 | 200.0 |
| 171A | 6.1 | 6.1 | 27.7 |
| 172A | 4.8 | 6.1 | 31.6 |
| 173A | 104.3 | 37.9 | |
| 174A | 18.8 | 14.3 | 55.8 |
| 175A | 18.2 | 10.9 | 65.1 |
| 176A | 6.4 | 4.9 | 29.0 |
| 177A | 8.8 | 4.5 | 21.1 |
| 178A | 4.9 | 7.5 | 47.7 |
| 179A | 7.2 | 7.6 | 25.6 |
| 180A | 9.3 | 4.9 | 16.8 |
| 181A | 8.4 | 7.4 | 26.4 |
| 182A | 8.0 | 7.1 | 22.3 |
| 183A | 18.4 | 4.9 | 42.1 |
| 184A | 28.9 | 5.3 | 94.8 |

Compounds of formula B showed the following activity in this assay:

| Compound | IC$_{50}$ (MX-1), μM | IC$_{50}$ (DLD-1), μM | IC$_{50}$ (LNCap), μM |
|---|---|---|---|
| 1B | 4.0 | 2.5 | 5.1 |
| 2B | 200 | 0.3 | 10.9 |
| 3B | 7.4 | 4.3 | 14.8 |
| 4B | 4.1 | 2.9 | 11.5 |
| 6B | 6.9 | 0.8 | 11.6 |
| 7B | 1.9 | 1.5 | 9.5 |
| 8B | 10.9 | 6.5 | 28.0 |
| 9B | 6.0 | 6.1 | 25.5 |
| 10B | 10.8 | 6.1 | 1.9 |
| 11B | 3.0 | 2.1 | 4.5 |
| 12B | 4.3 | 1.9 | 7.1 |
| 13B | 1.9 | 2.3 | 4.7 |
| 14B | 2.3 | 3.2 | 5.7 |
| 15B | 1.4 | 2.4 | 4.4 |
| 16B | 2.9 | 4.5 | 9.2 |
| 17B | 6.2 | 4.6 | 18.6 |
| 18B | 8.4 | 2.7 | 49.8 |
| 19B | 7.6 | 3.8 | 52.0 |
| 20B | 5.1 | 4.0 | 33.3 |
| 21B | 14.9 | 4.1 | 131.9 |
| 22B | 7.0 | 2.5 | 40.8 |
| 23B | 1.1 | 0.7 | 3.8 |

The compound of formula 1C showed the following activity in this assay:

| Compound | IC$_{50}$ (MX-1), μM | IC$_{50}$ (DLD-1), μM | IC$_{50}$ (LNCap), μM |
|---|---|---|---|
| 1C | 0.3 | 0.3 | 1.4 |

In Vitro Example 2

Cell Cycle Analysis

Log-phase DLD-1 cells were seeded in a 75-mL flask for several hours to allow cell attachment, with the seeding density chosen so that the cell culture would be less than 80% confluent on the day of harvest. The test compounds were added (dissolved in DMSO) at approximately IC$_{75-85}$ to achieve a final DMSO concentration of 0.1%, and the cells then incubated further for one and two days. Following incubation, the cells were harvested by trypsinization, fixed in 75% aqueous ethanol, and stored at −20° C. until further analysis. To determine the cellular DNA content, which reflects the cell cycle status, the fixed cells were washed twice with phosphate-buffered saline and then treated with RNase for 30 minutes at 37° C. They were then stained with the fluorescent dye propidium iodide, followed by FACS analysis on a Becton Dickinson FACSCalibur system. Similarly to canfosfamide, and in contrast to melphalan, both compounds 70A and 128A induced a G2/M cycle block in this assay. Other compounds of formula A and formula B were tested in this assay.

In Vitro Example 3

DNA Damage Assay

Lambda DNA (1 μg in 20 μL phosphate-buffered saline) was incubated with the test compounds (concentrations of 100 μM and 300 μM, dissolved in DMSO) at room temperature for one day, and the DNA then purified with the DNeasy kit. After quantitation by a plate assay using the SYBR-Gold assay (5 μL DNA+200 μL dye at 1:10,000 dilution in TE buffer), 250 pg of each sample were amplified by PCR using AmpliTaq Gold reagents and the primers 5'-ccg act ggc acc gct tt-3' and 5'-cag gcc acc atc acg cat-3', with PCR parameters 95° C., 10 min; 25 cycles of (95° C., 30 sec; 60° C., 30 sec; 72° C., 3 min); 72° C., 10 min; then holding the samples at 4° C. until analysis. The PCR products were quantitated by the same SYBR-Gold assay. Similarly to canfosfamide, and in contrast to melphalan, both compounds 70A and 128A showed only marginal DNA damage activity in this assay.

Other compounds of formula A and formula B were tested in this assay, and many showed only low amounts of DNA damage when compared to agents such as melphalan.

In Vitro Example 4

Cross-Resistance Assay

Cross-resistance between test compounds and anticancer agents are assayed by the use of matched cell line pairs, i.e. a standard cancer cell line and a derivative cell line that has been made resistant to a particular anticancer agent by culture in the presence of a sublethal concentration of the agent. Standard cytotoxicity assays are performed in each cell line, essentially as described in In vitro Example 1, and the resistance ratio, the ratio of the $IC_{50}$ for the derivative cell line to the $IC_{50}$ for the standard cell line is calculated. A test compound is considered cross-resistant with a selected anticancer agent if the resistance ratio for the test compound is approximately 2 or higher in cells resistant to the selected anticancer agent. Compounds 70A and 128A were not cross-resistant with doxorubicin in the P388 murine leukemia cell line. Other compounds of formula A and formula B were tested in this assay, and many were also not cross-resistant.

In Vitro Example 5

Synergism Assay

Synergism between test compounds and anticancer agents are assayed in a chosen cell line. Standard cytotoxicity assays are performed in the cell line, essentially as described in In vitro Example 1, using fixed or variable ratios of the test compound and the anticancer agent, with enhancement of cytotoxicity when the test compound is combined with an anticancer agent compared to either compound alone indicating synergism. The results can also be analyzed using the Combination Index (CI) method with the "CalcuSyn" program from Biosoft, with a CI value less than 1 indicating synergy, 1 indicating an additive effect, and greater than 1 indicating antagonism. Similarly to canfosfamide, compound 128A was seen to be synergistic with carboplatin in the OVCAR-3 cell line in this assay.

IN VIVO EXAMPLES

In Vivo Example 1

MX-1 Xenograft Assay, Intraperitoneal Administration

Female athymic nu/nu mice (Harlan, Indianapolis, Ind., U.S.A. or similar vendor), 6-8 weeks old (approximately 20 g), were implanted in the mammary fat pad of the right fore flank with 20-30 mg pieces of MX-1 (human breast cancer) tumor harvested from similar mice that had previously been implanted with the MX-1 tumor. Approximately 7-10 days after tumor transplantation, when the tumor weight was approximately 50-200 mg, the mice were assigned to treatment groups. Groups of mice were treated with compounds 5A, 13A, 15A, 23A, 70A, 128A, 171A, 172A, and 180A at 100 mg/Kg by intraperitoneal injection once/day for 5, 9, or 14 days, with vehicle control. All compounds were active in this assay, with tumor growth inhibition compared to vehicle between 5% (compound 171A) and 99% (compound 13A), with most compounds causing at least 30% tumor growth inhibition. Compounds 13A, 70A, and 128A were also tested over a range of doses and treatment times, and caused dose-dependent tumor inhibition. Compound 13A was tested at 25, 50, or 100 mg/Kg for 5 or 9 days, causing tumor inhibition between 19% (25 mg/Kg for 5 days) and 99% (100 mg/Kg for 9 days). Compound 70A was tested at 50, 100, and 150 mg/Kg for 5 or 12 days, causing tumor inhibition between 16% (50 mg/Kg for 5 days) and 95% (150 mg/Kg for 12 days).

In Vivo Example 2

MX-1 Xenograft Assay, Oral Administration

A study similar to that described in In vivo Example 1 was performed using oral administration of compounds 13A and 70A. Groups of mice were treated with compound 13A at 50, 100, or 300 mg/Kg, or compound 70A at 100, 150, 200, or 250 mg/Kg, by gavage once/day for 5 days (with vehicle control). Tumor growth inhibition was measured 13 days after the start of treatment. Both compounds were active in this assay and caused dose-dependent tumor inhibition. Compound 13A caused a dose-dependent inhibition of tumor growth between 63% (50 mg/Kg) and 100% (300 mg/Kg) compared to vehicle, and compound 70A caused a dose-dependent inhibition between 36% (at 100 mg/Kg) and 96% (250 mg/Kg).

In Vivo Example 3

HCT116 Xenograft Assay, Intraperitoneal Administration

Male athymic nu/nu mice, 6-8 weeks old (approximately 20 g), were implanted subcutaneously in the right fore flank with 20-30 mg pieces of HCT116 (human colon cancer) tumor harvested from similar mice that had previously been implanted with the HCT116 tumor. Approximately 7-10 days after tumor transplantation, when the tumor weight was approximately 50-200 mg, the mice were assigned to treatment groups. Groups of mice were treated with compounds 5A or 13A at 100 mg/Kg, or compound 70A at 150 mg/Kg, by intraperitoneal injection once/day for 11 days, with vehicle control. Tumor growth inhibition was measured 13 days after the start of treatment. All three compounds were active in this assay, with compound 5A causing 10% inhibition of tumor growth compared to vehicle, compound 13A causing 43% inhibition, and compound 70A causing 26% inhibition. A similar study of compounds 13A and 70A, using tumors started from tissue culture with 14 day compound administration and measurement 21 days after start of treatment, gave similar results.

In Vivo Example 4

MiaPaCa-2 Xenograft Assay, Intraperitoneal Administration

Male athymic nu/nu mice, 6-8 weeks old (approximately 20 g), were implanted subcutaneously in the right fore flank with 20-30 mg pieces of MiaPaCa-2 (human pancreatic cancer) tumor harvested from similar mice that had previously been implanted with the MiaPaCa-2 tumor. Approximately 7-10 days after tumor transplantation, when the tumor weight was approximately 50-200 mg, the mice were assigned to treatment groups. Groups of mice were treated with compound 13A or 70A at 100 mg/Kg by intraperitoneal injection once/day for 14 days, with vehicle control. Tumor growth inhibition was measured 15 days after the start of treatment.

Both compounds were active in this assay, with compound 13A causing 78% inhibition of tumor growth compared to vehicle and compound 70A causing 38% inhibition.

In Vivo Example 5

MiaPaCa-2 Xenograft Assay, Oral Administration

A study similar to that described in In vivo Example 4, but using oral administration of compounds 13A and 70A at 200 mg/Kg for 7 days, gave similar results to in vivo Example 4. Both compounds were active in this assay, with compound 13A causing 82% inhibition of tumor growth and compound 70A causing 27% inhibition.

All compounds tested were safe at the doses tested.

Formulation and therapeutic examples

Formulation Example 1

Formulation for Oral Administration

A solid formulation for oral administration is prepared by combining the following:

| | |
|---|---|
| Compound of this invention | 25.0% w/w |
| Magnesium stearate | 0.5% w/w |
| Starch | 2.0% w/w |
| Hydroxypropylmethylcellulose | 1.0% w/w |
| Microcrystalline cellulose | 71.5% w/w | and the mixture is compressed to form tablets or filled into hard gelatin capsules containing, for example, 100 mg of the compound of this invention. Tablets may be coated, if desired, by applying a suspension of a film-forming agent (for example, hydroxypropylmethylcellulose), pigment (for example, titanium dioxide), and plasticizer (for example, diethyl phthalate), and drying the film by evaporation of the solvent.

Formulation Example 2

Formulation for IV Administration

A formulation for IV administration is prepared by dissolving a compound of this invention, for example as a pharmaceutically acceptable salt, to a concentration of 1% w/v in phosphate-buffered saline; and the solution is sterilized, for example by sterile filtration, and sealed in sterile containers containing, for example, 100 mg of a compound of this invention.

Alternatively, a lyophilized formulation is prepared by dissolving a compound of this invention, again for example as a pharmaceutically acceptable salt, in a suitable buffer, for example the phosphate buffer of the phosphate-buffered saline mentioned above, sterilizing the solution and dispensing it into suitable sterile vials, lyophilizing the solution to remove the water, and sealing the vials. The lyophilized formulation is reconstituted by the addition of sterile water, and the reconstituted solution may be further diluted for administration with a solution such as 0.9% sodium chloride intravenous infusion or 5% dextrose intravenous infusion.

Therapeutic Example

Therapy with Compounds of this Invention

A compound of this invention, diluted in 5% dextrose intravenous infusion, is administered intravenously over 30 minutes to a patient suffering from metastatic ovarian carcinoma at an initial dose of 100 mg/m$^2$; and this dose is increased to 250 mg/m$^2$, 500 mg/m$^2$, 750 mg/m$^2$, and 1000 mg/m$^2$. The compound is administered at 1-week intervals. The same dose escalation is administered at 2- and 3-week intervals to other patients suffering from the same cancer.

While this invention has been described in conjunction with specific embodiments and examples, it will be apparent to a person of ordinary skill in the art, having regard to that skill and this disclosure, that equivalents of the specifically disclosed materials and methods will also be applicable to this invention; and such equivalents are intended to be included within the following claims.

We claim:

1. A compound of formula:

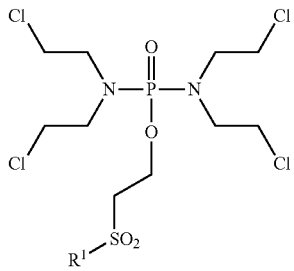

where:

R$^1$ is alkyl, optionally substituted with one to three groups selected from —OH, —C(O)OH, —SO$_2$OH,

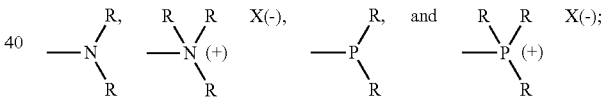

each R is independently hydrogen, optionally R'-substituted alkyl, optionally R'-substituted heteroalkyl, optionally R'-substituted aryl, optionally R'-substituted heteroaryl, optionally R'-substituted aralkyl, optionally R'-substituted heteroaralkyl, or two R groups form a 4- or 5-member optionally R'-substituted alkanediyl or optionally R'-substituted heteroalkanediyl;

each R' is, independently, 1 to 3 substituents selected from halo, —SH, —NH$_2$, or —C(O)Oalkyl; and X is a halogen;

or its pharmaceutically acceptable salt.

2. A pharmaceutical composition comprising the compound of claim 1 and an excipient.

3. The compound of claim 1, wherein R$^1$ is alkyl, optionally substituted with one to three groups selected from —OH, —C(O)OH, and —NR$_2$; and each R is independently hydrogen or alkyl;

or its pharmaceutically acceptable salt.

4. A pharmaceutical composition comprising the compound of claim 3 and an excipient.

* * * * *